(12) United States Patent
Van Wyk et al.

(10) Patent No.: US 10,188,417 B2
(45) Date of Patent: Jan. 29, 2019

(54) PERCUSSIVE SURGICAL DEVICES, SYSTEMS, AND METHODS OF USE THEREOF

(71) Applicant: Tenjin LLC, Brazoria, TX (US)

(72) Inventors: Robert A. Van Wyk, St. Pete Beach, FL (US); Gary R. Heisler, Brazoria, TX (US); Christopher P. Dougherty, Rogers, AR (US)

(73) Assignee: Tenjin, LLC, Brazoria, TX (US)

( * ) Notice: Subject to any disclaimer, the term of this patent is extended or adjusted under 35 U.S.C. 154(b) by 0 days.

(21) Appl. No.: 15/793,504

(22) Filed: Oct. 25, 2017

(65) Prior Publication Data

US 2018/0055527 A1     Mar. 1, 2018

Related U.S. Application Data

(63) Continuation of application No. 14/582,232, filed on Dec. 24, 2014, now Pat. No. 9,833,255.

(60) Provisional application No. 61/964,180, filed on Dec. 26, 2013.

(51) Int. Cl.
| | |
|---|---|
| *A61B 17/32* | (2006.01) |
| *A61B 17/04* | (2006.01) |
| *A61B 17/92* | (2006.01) |
| *A61B 17/16* | (2006.01) |

(52) U.S. Cl.
CPC .... *A61B 17/32002* (2013.01); *A61B 17/0401* (2013.01); *A61B 17/1604* (2013.01); *A61B 17/92* (2013.01); *A61B 17/1675* (2013.01); *A61B 2017/0409* (2013.01); *A61B 2017/0427* (2013.01); *A61B 2017/0445* (2013.01); *A61B 2017/320028* (2013.01)

(58) Field of Classification Search
CPC .. A61B 2017/1604; A61B 2017/32002; A61B 2017/320028; A61B 2017/0409; A61B 17/0401
See application file for complete search history.

(56) References Cited

U.S. PATENT DOCUMENTS

| | | | |
|---|---|---|---|
| 2007/0219557 A1* | 9/2007 | Bourque | A61B 17/0401 606/326 |
| 2008/0058816 A1* | 3/2008 | Philippon | A61B 17/0401 606/326 |
| 2008/0132932 A1 | 6/2008 | Hoeppner | |
| 2009/0062742 A1* | 3/2009 | Rotella | A61B 17/0401 604/192 |
| 2010/0076440 A1 | 3/2010 | Pamichev | |
| 2010/0249786 A1 | 9/2010 | Schmieding | |

(Continued)

*Primary Examiner* — Olivia C Chang
(74) *Attorney, Agent, or Firm* — Chalin A. Smith; Smith Patent, LLC

(57) ABSTRACT

In the context of bone surgery and in particular arthroscopic surgery, there is frequently a need for the application of "percussive force" to the distal end component(s) of a surgical device, i.e., repetitive percutient or striking force analogous to that of a hammer driving a nail. Disclosed herein are mechanisms and methods for automating and/or controlling the application of such a percussive force so as to avoid the present need in the art for a "third hand". The present invention addresses the significant and long felt need by providing a powered percussive driver device that may be controlled directly by the primary surgeon.

22 Claims, 33 Drawing Sheets

(56) References Cited

U.S. PATENT DOCUMENTS

2013/0035692 A1\* 2/2013 Sorensen ........... A61B 17/0401
606/87
2014/0172016 A1\* 6/2014 Housman ........... A61B 17/0401
606/232

\* cited by examiner

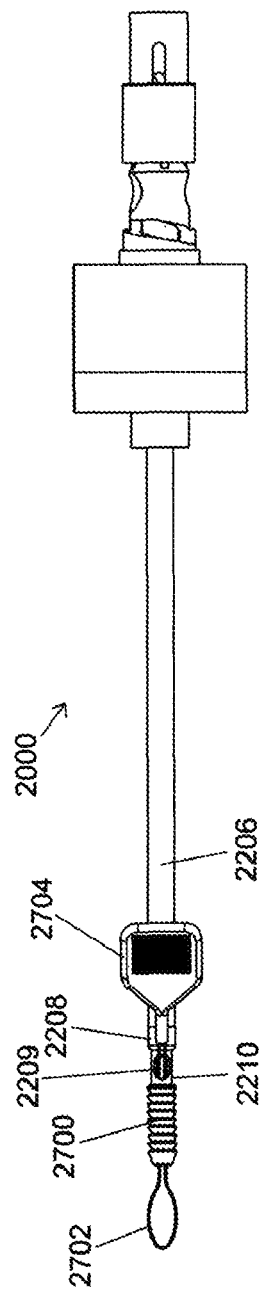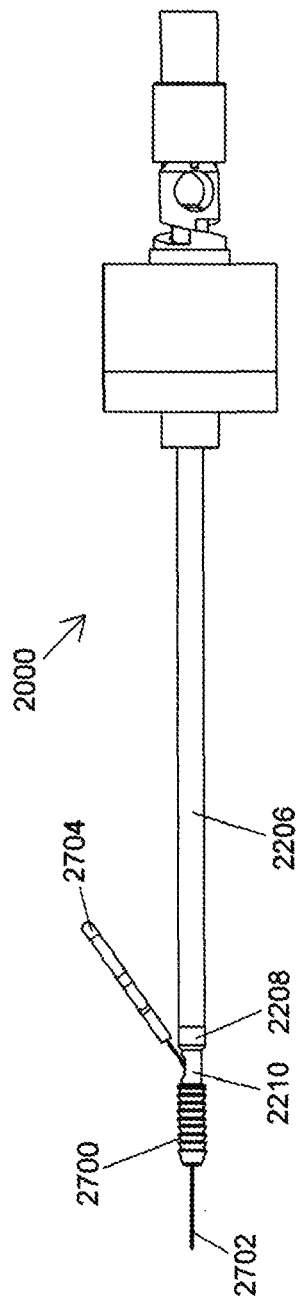
Fig. 42
Fig. 43

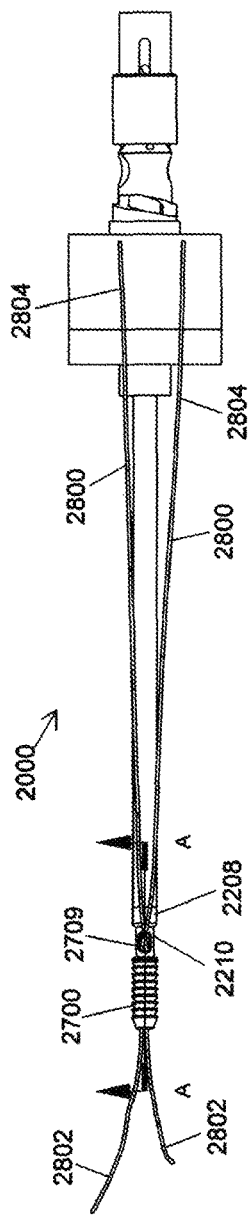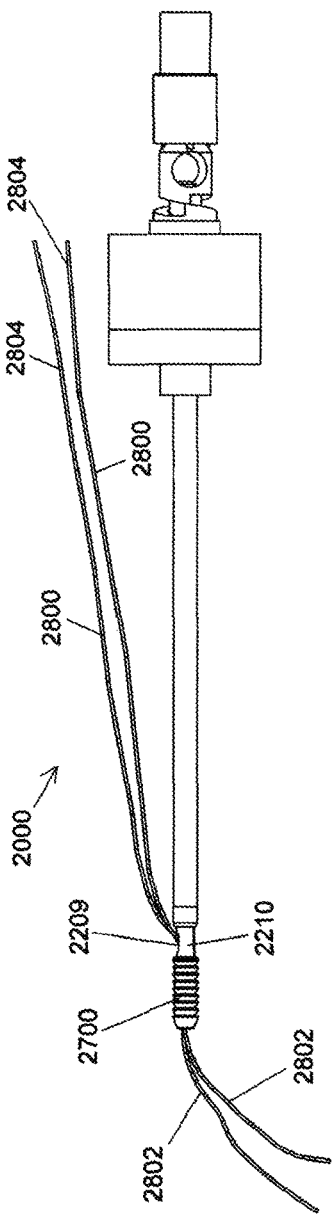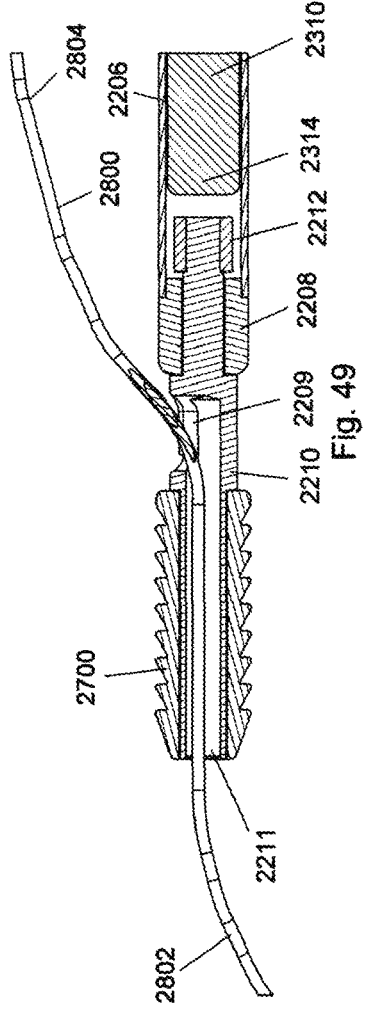

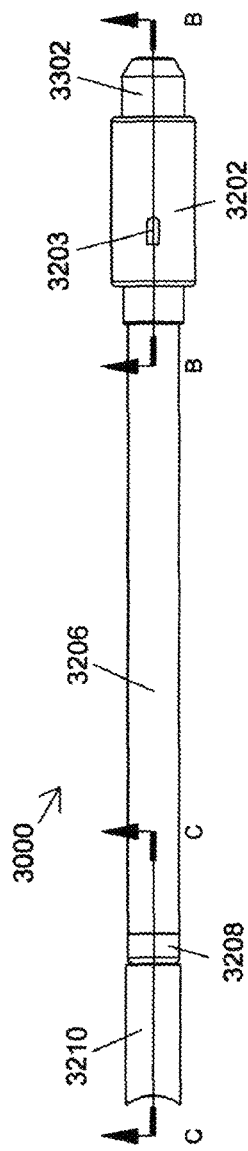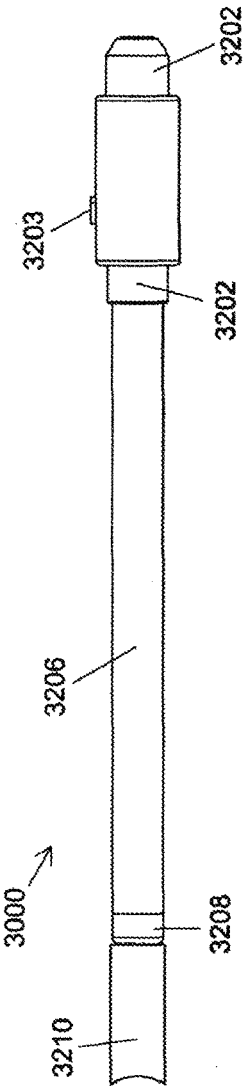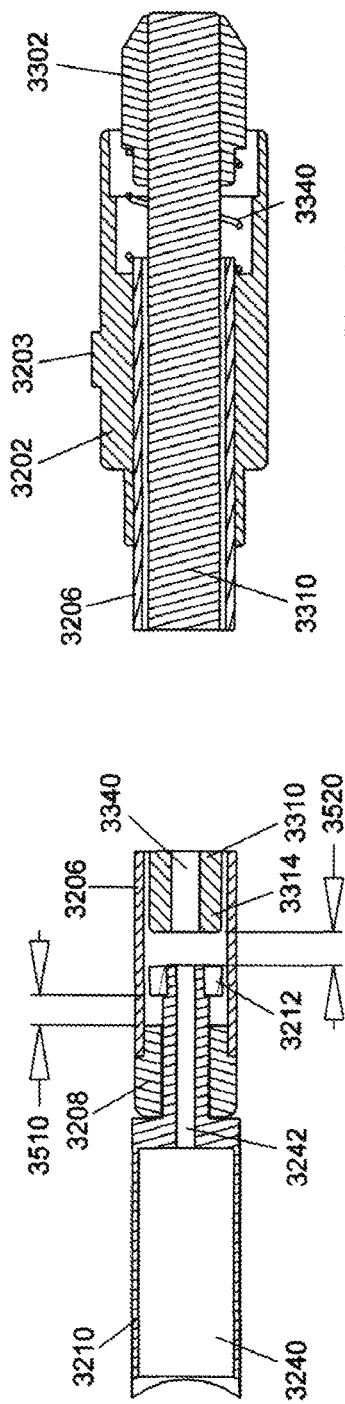

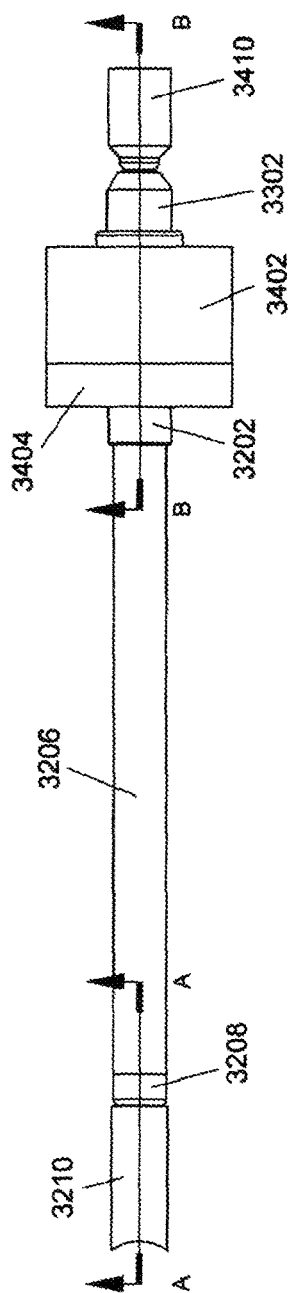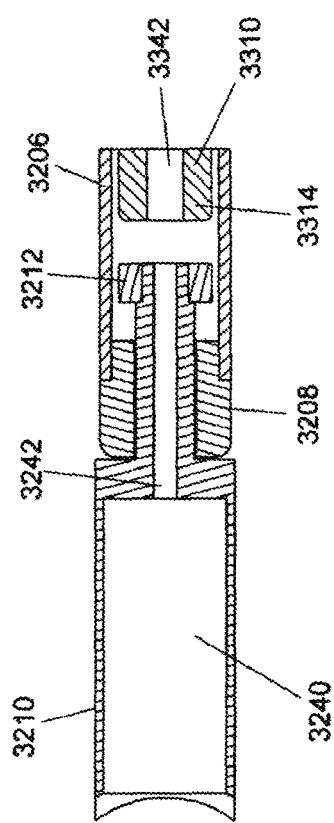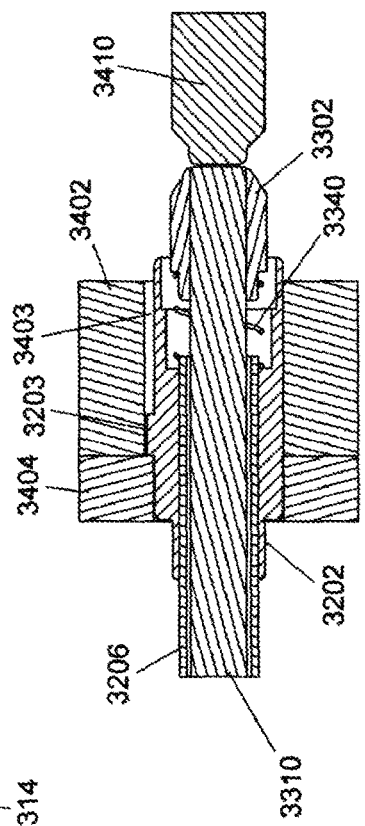

PERCUSSIVE SURGICAL DEVICES, SYSTEMS, AND METHODS OF USE THEREOF

PRIORITY

This application is a continuation of U.S. patent application Ser. No. 14/582,232 filed Dec. 24, 2014, which, in turn, claims the benefit of U.S. Provisional Application No. 61/964,180 filed Dec. 26, 2013, the contents of which are hereby incorporated by reference in their entirety.

FIELD OF THE INVENTION

The present invention relates generally to the field of endoscopic surgery and powered surgical instruments for use therein. More particularly, the invention relates to a minimally invasive endoscopic percussive driver for producing indentations in bony surfaces or driving implants into bone. In the context of the present invention, the rotational motion of a device such as an arthroscopy shaver handpiece is converted into percussive energy usable for surgical applications.

BACKGROUND OF THE INVENTION

Many surgical procedures, and in particular arthroscopic surgeries, require the application of "percussive force", i.e., repetitive percutient or striking force. In the typical case, the percussive force (or energy) is supplied by a mallet striking a proximal portion of a device requiring such application, such as a surgical awl. In a first instance the percussive force may be required to drive the distal portion of the awl into a bony surface so as to form the recesses required for the microfracture treatment of an articular lesion. In another instance, the percussive force may be applied to the proximal end of a driver used to place an interference plug implant (also called an "anchor") for the purpose of securing a tissue graft to a bony surface. In the context of arthroscopic surgery, the surgeon often needs to manipulate an endoscope so as to maintain visualization of the surgical site while also controlling a device introduced for its clinical effect. As a result, both hands of the surgeon are usually occupied and thus it is necessary that a third hand to apply the percussive force (e.g., the mallet to the device) to achieve the desired clinical effect. This has certain distinct drawbacks. First of all, it means that every surgery requires a minimum of a surgeons plus a skilled medical professional. Second, application of an external percussive force, especially in the form of a striking mallet, by another person places the surgeon's hands at some risk for injury. Finally, the degree of precision of the result may be compromised by the application of excess force by the mallet wielder.

Accordingly, there is a need for a powered percussive loading device that may be controlled directly by the primary surgeon. The present invention addresses this significant and long felt need by providing a control mechanism, for example in the form of a foot pedal or hand control on the interventional surgical device itself.

SUMMARY OF THE INVENTION

A primary goal of the present invention is to provide means and methods for automating and/or controlling the application of the requisite percussive force that frequently accompanies surgical procedures, such as arthroscopic surgeries, so as to avoid the present need in the art for the "third hand" in such context. To that end and accordance with that goal, it is an objective of the present invention to provide a percussive surgical device, for example as herein described and comprising:

a. an outer assembly characterized by (i) a proximal outer hub having proximal and distal ends, wherein the proximal end of the outer hub includes a first cooperating element, and (ii) a distal tubular portion having proximal and distal ends and an elongate lumen extending therebetween, wherein the proximal end of the distal tubular portion is configured to the distal end of the outer hub and the distal end of the distal tubular portion includes a distally projecting penetrating element positioned and axially movable within the elongate lumen; and b. an inner assembly characterized by (i) a proximal inner hub having proximal and distal ends, wherein the proximal end of the inner hub includes a drive portion for transmitting rotational motion from an external shaver handpiece to the inner assembly, and the distal end of the inner hub includes a second cooperating element that engages the first cooperating element, and (ii) a distal portion comprising an elongate driving rod slidably positioned and rotationally and axially movable within the elongate lumen of the distal tubular portion of the outer assembly;

wherein:
the proximal end of the outer hub is connected to the distal end of the inner hub; and
the drive portion of the inner hub further comprises an elastic member that transmits an axial force distally on the inner member to maintain the engagement of the first and second cooperating elements when the inner member hub and outer member hubs are connected;

whereby:
rotation of the inner assembly relative to the outer assembly drives an interaction between the first and second cooperating elements which causes the inner assembly to move axially from a first extended position to a second retracted position while simultaneously compressing the elastic member; and
rotation of the respective inner and outer assemblies past a pre-determined stop limit results in a release of the compressed elastic member, which, in turn, propels the inner assembly in distal direction such that the distal end of the driving rod strikes the proximal end of the distally projecting penetrating element with a percussive force sufficient it to move axially in the distal direction.

It is a further objective of the present invention to provide a percussive arthroscopic shaver assembly, for example as herein described and comprising an arthroscopy shaver handpiece having a distal end defining the opening of a central lumen and a proximal end characterized by a rotational drive element, assembly to the above-described percussive surgical device, wherein the outer assembly is received with the central lumen such that rotation of the distal rotational drive element causes rotation of the inner assembly.

It is yet a further objective of the present invention to provide a method for producing a plurality of microfractures in a bony surface in a patient in need thereof using, for example, the above-described percussive arthroscopic shaver assembly, for example as herein described and comprising the following steps:

a. introducing the percussive arthroscopic shaver assembly into a target surgical site comprising the bony surface of interest;
b. positioning the distally projecting penetrating element of the outer assembly of the percussive surgical device against the bony surface;
c. rotating the distal rotational drive element of the arthroscopic shaver handpiece so as to cause rotation of the inner assembly relative to the outer assembly, which, in turn, causes the inner assembly to axially move from a first extended position to a second retracted position while simultaneously compressing the elastic member;
d. continuing to rotate the respective inner and outer assemblies past a pre-determined stop limit so as to cause release of the elastic member, which, in turn, propels the inner assembly in distal direction such that the distal end of the driving rod strikes the proximal end of the distally projecting penetrating element with a percussive force sufficient it to move axially in the distal direction; and
e. repeating steps (c) and (d) as needed until a plurality of microfractures are formed in the bony surface.

Such a method finds utility in connection with arthroscopic knee repair, for example.

Aspects and embodiments of the present invention in accordance with the afore-noted objectives are as follows:

In a first aspect, the present invention relates to a surgical device and method for converting the rotary motion of a conventional shaver handpiece to percussive energy, which is then transmitted to an axially movable distal element. In an illustrative embodiment, such a device has an elongate distal portion housing the interventional component(s) and a proximal portion that includes inner and outer hubs for removable mounting of the device to the handpiece.

In a particularly preferred embodiment, a proximal portion of the outer hub has formed thereon a helical cam element with proximally facing cam surfaces that coordinates with mating cam surface(s) on a distal portion of the inner hub. Distal surface(s) of the inner hub are configured to follow the cam surface of the outer hub so as to create axial relative motion between the inner and outer hubs and the assemblies to which they are affixed. A spring mounted to the device provides the distal axial force between the inner hub and handpiece necessary to maintain contact between the cam and follower surfaces of the inner and outer hubs. The cam components are constructed such that rotation of the inner member causes compression of the spring to a predetermined limit whereupon further rotation allows the inner assembly to freely advance distally, propelled by the compressed spring. In this manner, rotational energy supplied to the device by the handpiece is converted to stored energy in the spring, and, upon release by the cam, to kinetic energy as the inner assembly is propelled distally by the spring force. Distal to the inner hub and affixed thereto is an inner assembly that includes an elongate rod member of predetermined mass. Coaxial with the elongate rod member of the inner assembly is an outer assembly that includes an outer tubular member having a proximal end attached to the outer hub and a distal end that includes a cannulated element affixed thereto. Positioned within the lumen of the distal end cannulated element is an axially movable distal element that freely moves between a first proximal position and a second distal position. When in the second distal position, the distal end of the axially movable distal element protrudes beyond the distal limit of the cannulated element. The protruding distal end of the axially movable distal element may optionally be configured for penetration into a bony surface, or, alternatively, may be configured for transmitting percussive energy to an implant that is to be inserted into bone. The maximum travel of the axially movable element between its first proximal position and second distal position (i.e., between its proximal and distal limits) is configured to be less than the travel of the inner assembly within the outer assembly caused by the cooperative interaction of the cam and follower. Because of this, the inner assembly rod element travels freely and is accelerated by the stored spring force until the distal end of the rod element contacts the proximal end of the axially movable distal element of the outer assembly so as to percussively transmit energy thereto. If the distal portion of the axially movable distal element is configured for penetration of bone and the distal end thereof is in contact with a bony surface, the repeated application of this percussive force will cause incremental penetration of the distal portion of the movable element into the bone, much like repeated strikes against a hammer drive the insertion of a nail into a substrate of interest. Alternatively, if the distal portion of the axially movable distal element is configured for the placement of an implant, incremental distal advancement of the implant into the bone will occur. In either case, the device of the present invention adaptively converts the rotational energy of the shaver handpiece first to stored spring energy, then to kinetic energy of a rod element that is percussively applied to the proximal side of the axially movable distal element where it is then dissipated in achieving a desired clinical effect. The percussive energy that may be dissipated in achieving the clinical effect is limited by the maximum axial travel of the inner assembly within the shaver handpiece and by the maximum constant of the spring that can be compressed by the shaver handpiece. In this manner, both the duration and power of the percussive force may be strictly controlled so as to avoid damage (to the patient or the surgeon) that can result from overstrike.

A second aspect of the present invention relates to a percussive surgical system that includes a removable device for transmitting percussive energy to an axially movable distal element, and a handpiece configured to provide percussive energy to the device. Because the percussive energy source is a handpiece designed for the production of percussive energy, the limitations on maximum percussive energy available for producing clinical effects due to the use of a shaver handpiece are eliminated. Such a system finds particularly utility in the context of clinical applications that require greater percussive energy. For instance, devices of the instant invention system may be used to produce holes having non-circular geometries that cannot be produced by a rotary drill. Such holes may be used as sockets for the placement of implants having optimized non-radial forms.

These and other aspects are accomplished in the invention herein described, directed to a powered percussive surgical device. Further objects and features of the invention will become more fully apparent when the following detailed description is read in conjunction with the accompanying figures and examples. To that end, other embodiments of the percussive surgical device of the present invention may include or utilize manual instruments that convert energy input by the surgeon to percussive energy applied to a distal element. For example, in one such embodiment, a force applied by the surgeon to an element of the device may compress an elastic member, such as a coil spring, that is attached to an axially movable weight. When the elastic element reaches a predetermined degree of compression, the compression mechanism is released so as to allow the weight to travel distally, propelled by energy supplied by the elastic member. The weight continues distally until striking a distal element thereby transferring percussive energy thereto. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention.

BRIEF DESCRIPTION OF THE FIGURES

Various aspects and applications of the present invention will become apparent to the skilled artisan upon consideration of the brief description of figures and the detailed description of the present invention and its preferred embodiments that follows:

FIG. 42 is a plan view of the objects of FIG. 41.

FIG. 43 is a side elevational view of the objects of FIG. 41.

FIG. 47 is a plan view of the objects of FIG. 46.

FIG. 48 is a side elevational view of the objects of FIG. 46.

FIG. 49 is an expanded sectional view of the objects of FIG. 47 at location A-A.

FIG. 57 is a plan view of the objects of FIG. 54.

FIG. 58 is a side elevational view of the objects of FIG. 54.

FIG. 59 is an expanded sectional view of the objects of FIG. 57 at location C-C.

FIG. 60 is an expanded sectional view of the objects of FIG. 57 at location B-B.

FIG. 61 is a plan view of the embodiment of FIG. 54 with elements of a handpiece configured to supply percussive energy to the device, and with the device in its retracted (first proximal) position.

FIG. 62 is an expanded sectional view of the objects of FIG. 61 at location A-A of FIG. 61.

FIG. 63 is an expanded sectional view of the objects of FIG. 61 at location B-B of FIG. 61.

DESCRIPTION OF THE PREFERRED EMBODIMENTS

Figure 1:
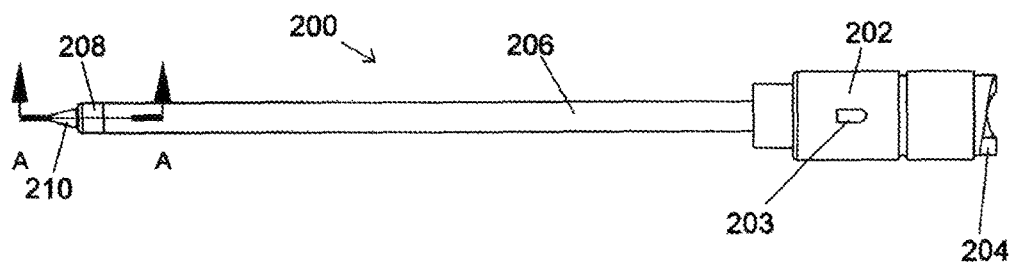
FIG. 1 depicts an illustrative outer assembly for a surgical percussive driver constructed in accordance with the principles of this invention.
Figure 2:
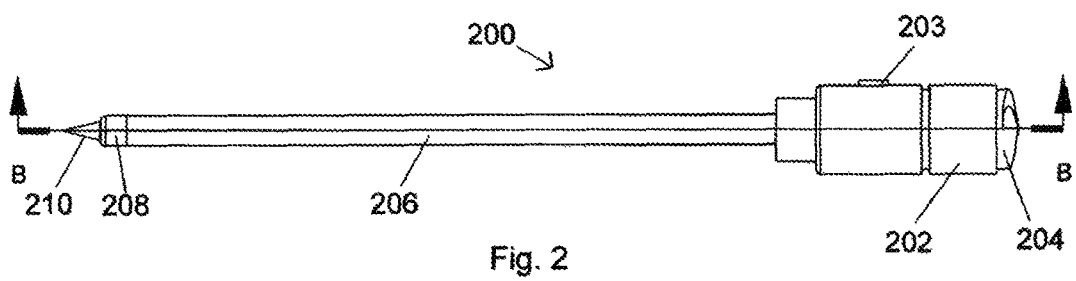
FIG. 2 is a side elevational view of the objects of FIG. 1.
Figure 3:
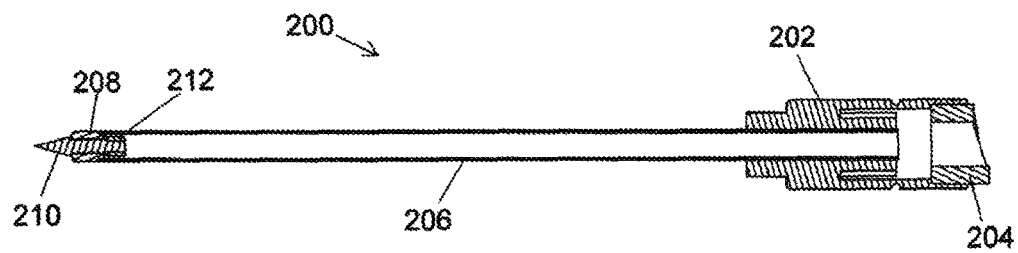
FIG. 3 is a side elevational sectional view of the objects of FIG. 1 at location A-A of FIG. 2.
Figure 4:
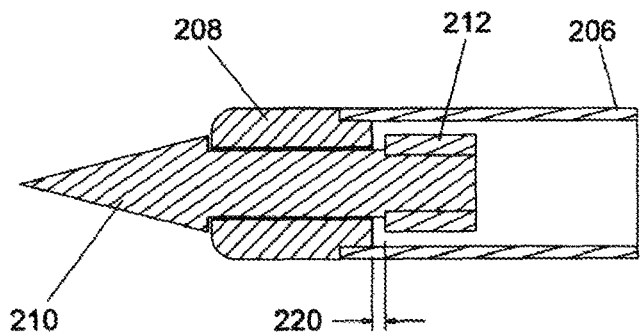
FIG. 4 is an expanded side elevational sectional view of the objects of FIG. 1 at location A-A of FIG. 1.
Figure 5:
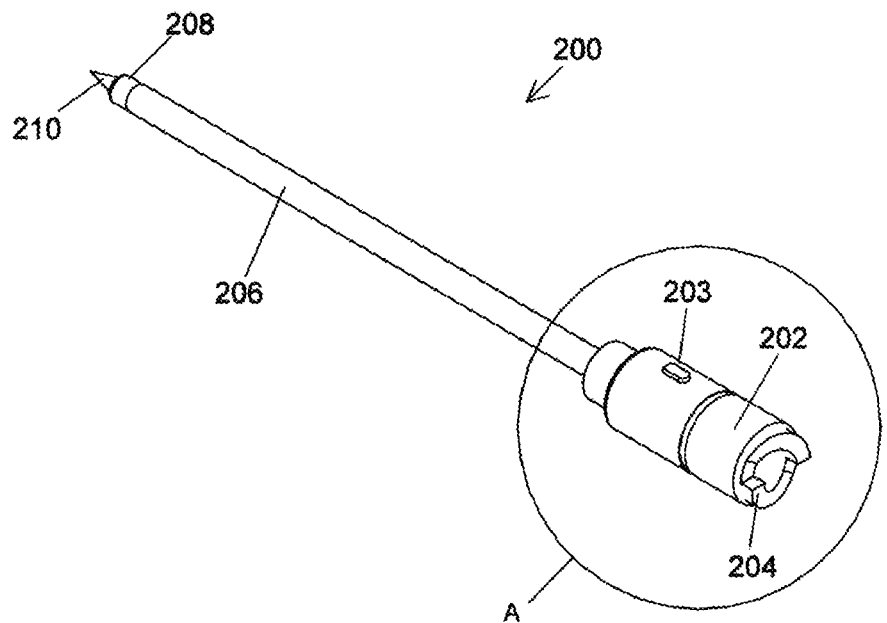
FIG. 5 is a perspective view of the objects of FIG. 1.
Figure 6:
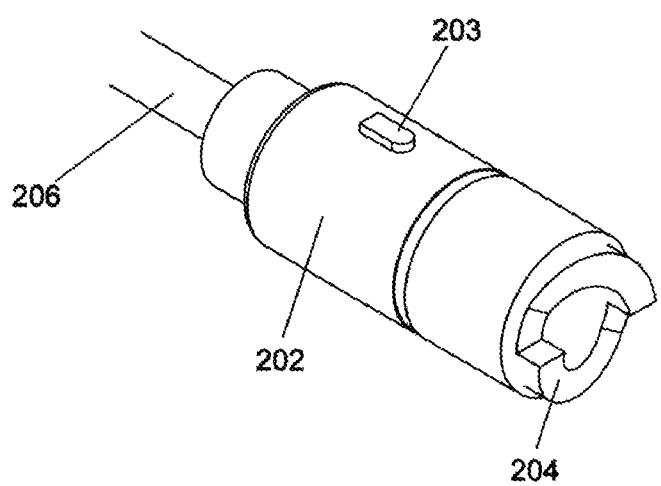
FIG. 6 is an expanded view of the proximal portion of the objects of FIG. 5.
Figure 7:
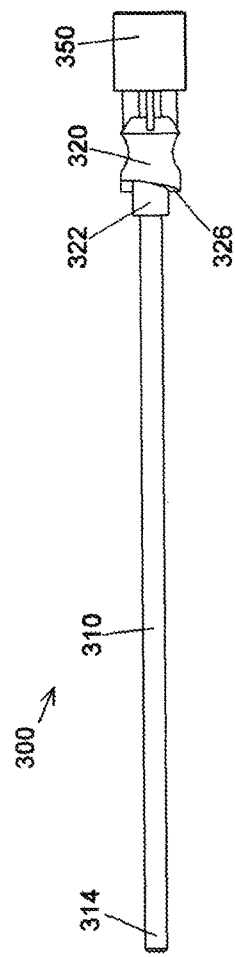
FIG. 7 is a plan view of an illustrative inner assembly for a surgical percussive driver constructed in accordance with the principles of this invention.
Figure 8:
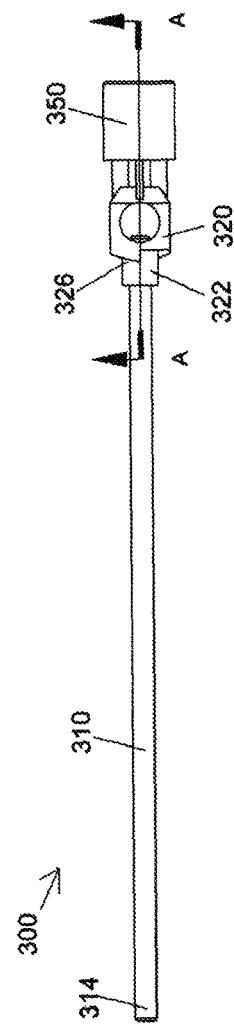
FIG. 8 is a side elevational view of the objects of FIG. 7.
Figure 9:
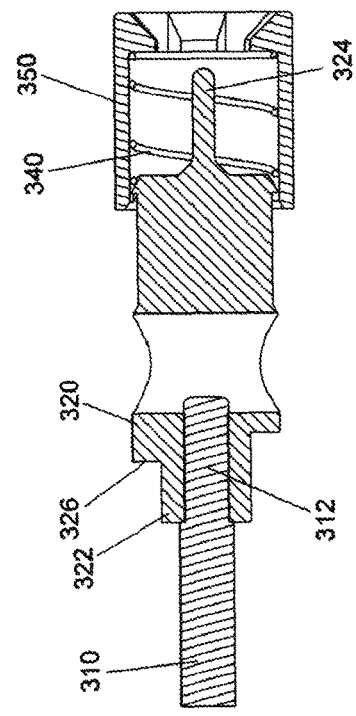
FIG. 9 is an expanded side elevational sectional view of the proximal portion of the objects of FIG. 7 at location A-A of FIG. 8.
Figure 10:
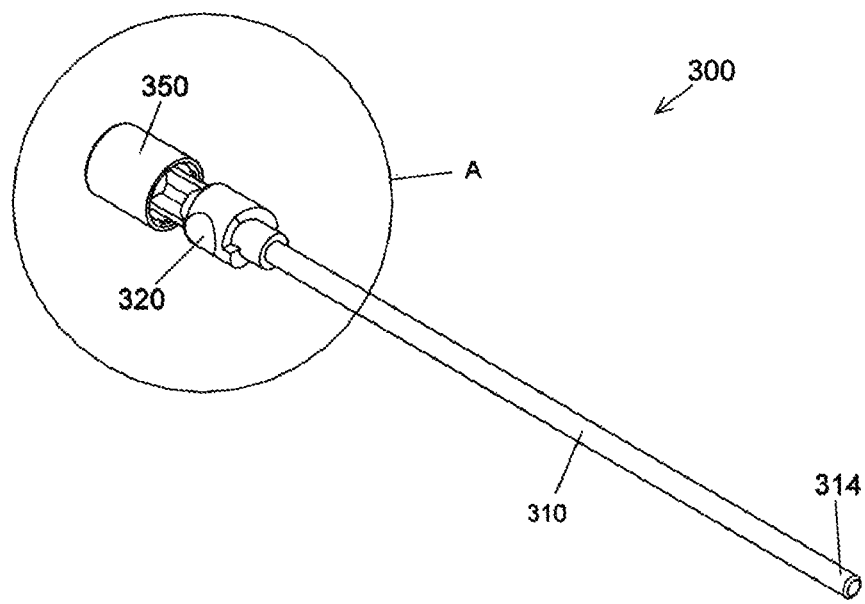
FIG. 10 is a distal perspective view of the objects of FIG. 7.
Figure 11:
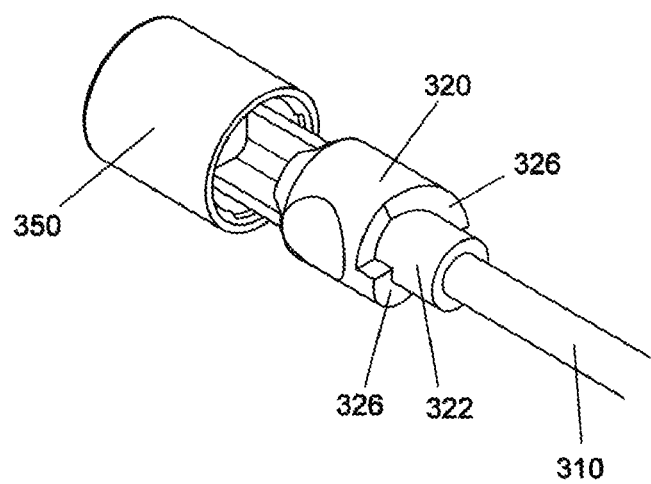
FIG. 11 is an expanded view of the proximal portion of the objects of FIG. 10
Figure 12:
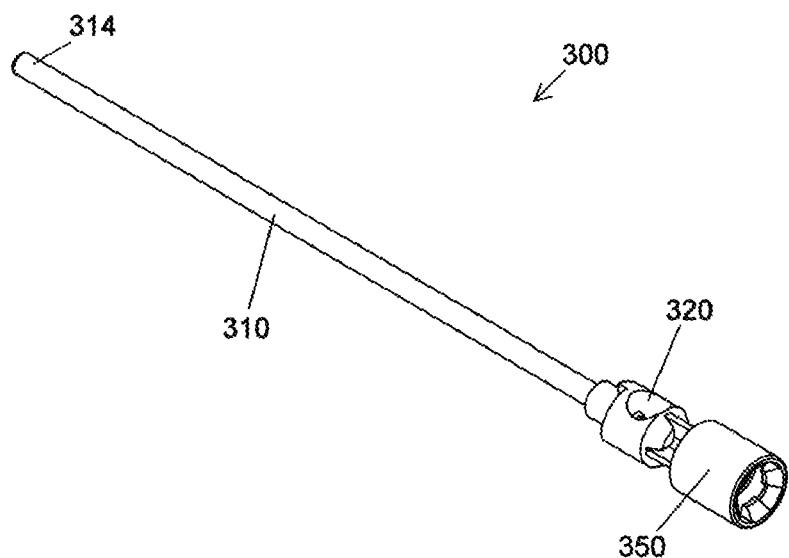
FIG. 12 is a proximal perspective view of the objects of FIG. 7.
Figure 13:
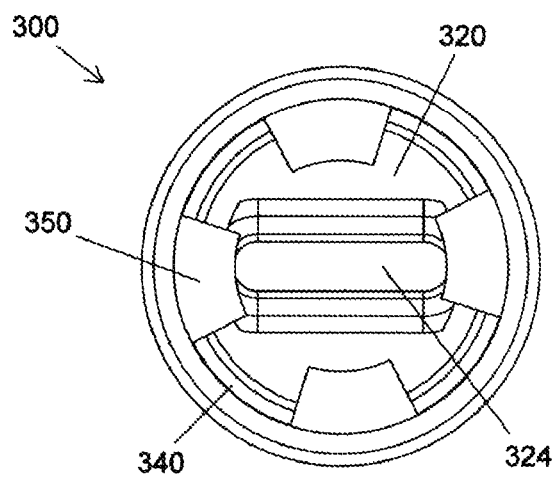
FIG. 13 is an expanded proximal axial view of the objects of FIG. 7.
Figure 14:
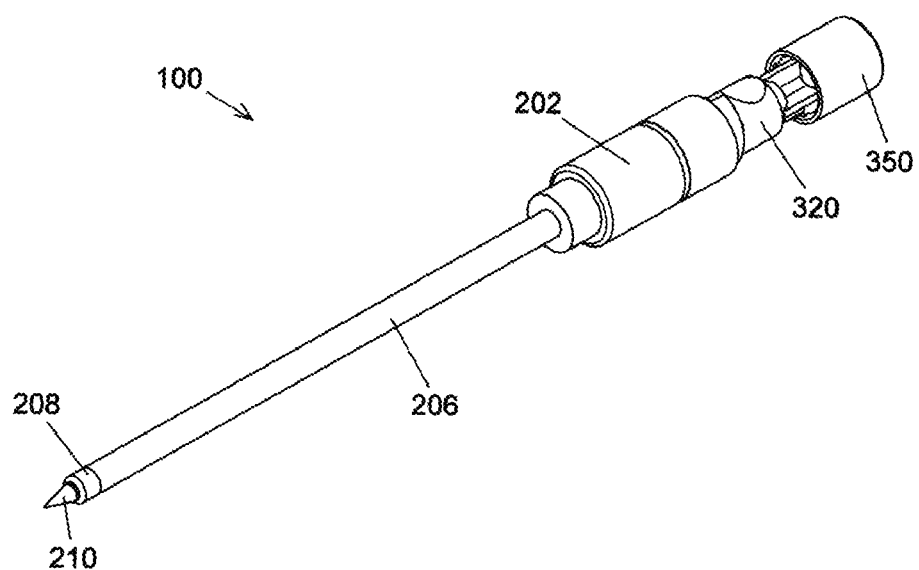
FIG. 14 is a distal perspective view of an illustrative surgical percussive driver constructed in accordance with the principles of this invention, including the inner assembly of FIG. 7 fitted with the outer assembly of FIG. 1.
Figure 15:
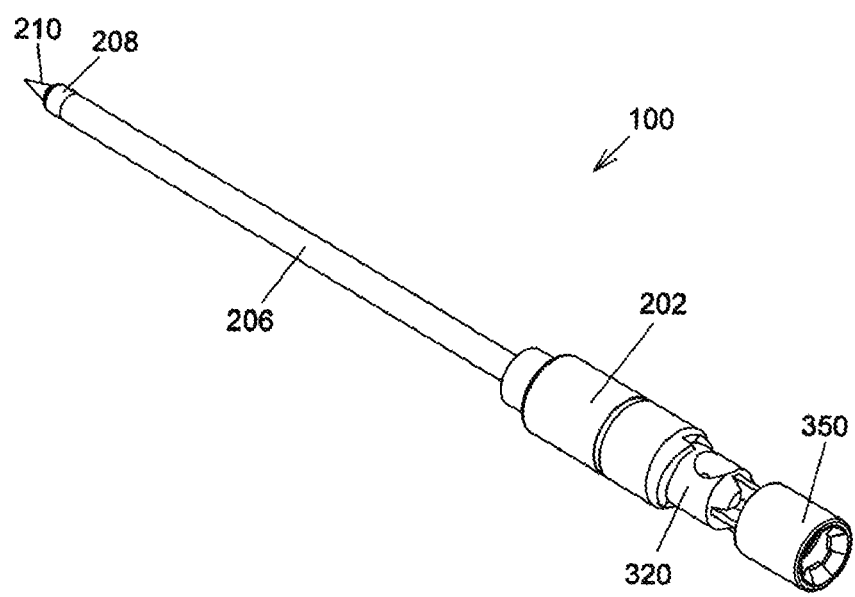
FIG. 15 is a proximal perspective view of the objects of FIG. 14.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control.

In the context of the present invention, the following definitions apply:

The words "a", "an" and "the" as used herein mean "at least one" unless otherwise specifically indicated. Thus, for example, reference to an "opening" is a reference to one or more openings and equivalents thereof known to those skilled in the art, and so forth.

The term "proximal" as used herein refers to that end or portion which is situated closest to the user of the device, farthest away from the target surgical site. In the context of the present invention, the proximal end of the powered percussive device includes the hub region.

The term "distal" as used herein refers to that end or portion situated farthest away from the user of the device, closest to the target surgical site. In the context of the present invention, the distal end of the powered percussive device includes the axially movable distal element optionally configured for penetration of a bony surface.

In the context of the present invention, the term "cannula" is used to generically refer to the family of elongate lumened surgical instruments that facilitate access across tissue to an internally located surgery site.

The terms "tube" and "tubular" are interchangeably used herein to refer to a generally round, long, hollow component having at least one central opening often referred to as a "lumen".

The terms "lengthwise" and "axial" as used interchangeably herein to refer to the direction relating to or parallel with the longitudinal axis of a device. The term "transverse" as used herein refers to the direction lying or extending across or perpendicular to the longitudinal axis of a device.

The term "lateral" pertains to the side and, as used herein, refers to motion, movement, or materials that are situated at, proceeding from, or directed to a side of a device.

The term "medial" pertains to the middle, and as used herein, refers to motion, movement or materials that are situated in the middle, in particular situated near the median plane or the midline of the device or subset component thereof.

The term "rotational" as used herein refers to the revolutionary movement about the center point or longitudinal axis of the device. In the context of the present invention, the inner assembly is rotated relative to the outer assembly, which typically is held in a stationary position, or vice versa. In either case, the rotary motion results in an energy potential that is stored and then subsequently transformed into an axial percussive force having clinical utility.

In the Summary above and the Examples below, the present invention makes reference to the use of a linear spring to store and subsequently release kinetic energy in the form of a percussive force. However, the present invention contemplates other compressible and/or elastomeric configurations for potential energy storage, i.e., alternative mechanisms, such as a bow or torsional spring, that may be deformed under pressure, tension or compression (i.e., stressed) and then subsequently released from stress, thereby transforming the stored energy into a kinetic energy that may be directed to a target location or component as a percussive force.

In the Examples below, the present invention makes reference to various lock-and-key type alignment mechanisms that serve to establish and secure the arrangement of the various device components, such as the outer assembly to the arthroscopy handpiece. It will again be readily understood by the skilled artisan that the position of the respective coordinating elements (e.g., mating slots and protrusions) may be exchanged and/or reversed as needed.

In the Summary above and the Examples below, the present invention makes reference to a "cam" and "cam surfaces". In the context of the present invention, a cam is a rotating or sliding piece in a mechanical linkage used especially in transforming rotary motion into linear motion or vice-versa. It is often a part of a rotating wheel (e.g. an eccentric wheel) or shaft (e.g. a cylinder with an irregular shape) that strikes a lever at one or more points on its circular path. The cam can be a simple tooth, as is used to deliver pulses of power to a steam hammer, for example, or an eccentric disc or other shape that produces a smooth reciprocating (back and forth) motion in the follower, which is a lever making contact with the cam.

The present invention contemplates the use of alternative cooperating elements for automatically transmitting relative axial movement when the inner and outer hubs are relatively rotated, in particular cooperating elements disposed on or within the inner and outer hubs. Examples of such cooperating elements include, but are not limited to, screw threads, worm gears, worm wheels, pneumatic devices, hydraulic mechanisms, magnetic assemblies, ratchet-and-pawl assemblies, and push-pull connectors.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal.

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to arthroscopic procedures, it is readily apparent that the teachings of the present invention may be applied to other minimally invasive procedures and are not limited to arthroscopic uses alone. As such, methods and materials similar or equivalent to those described herein can be used in the practice or testing of the present invention.

Examples

FIGS. 1 through 6 depict an outer assembly 200 for a surgical percussive driver constructed in accordance with the principles of this invention. Assembly 200 has a polymeric proximal portion forming a hub 202 with alignment key 203 for mounting in an arthroscopy shaver handpiece. A tubular cam element 204 having a helically formed proximal surface is mounted in the proximal end of hub 202. Outer assembly 200 has a distal tubular portion 206 terminating in a distal sub-assembly having a fixed portion 208 mounted to the distal end of tubular portion 206 and an axially movable portion formed of distal penetrating element 210 together with tubular retaining element 212 mounted to the proximal end of element 210 that acts as a stop mechanism, preventing the dislodgment or removal of the penetrating element 210 from the lumen of tubular portion 206. Distal penetrating element 210 can move axially distance 220 within element 208.

FIGS. 7 through 16 depict an inner assembly 300 for a surgical percussive driver constructed in accordance with the principles of this invention. Assembly 300 has a proximal portion including a polymeric hub 320 with a proximal end drive portion 324 for transmitting rotational motion provided by an arthroscopy shaver handpiece, and a distal portion 322 in which is mounted the proximal end 312 of metallic distal rod element 310, distal rod element 310 having a distal end 314. Hub 320 has mounted to its proximal drive portion spring 340 which has an initial compression supplied by, and is maintained in its position by spring retainer 350. Hub 320 has a helical distal-facing surface 326 having a pitch equal to that of the helical proximal surface of cam element 204 (FIGS. 1 through 6).

Figure 16:
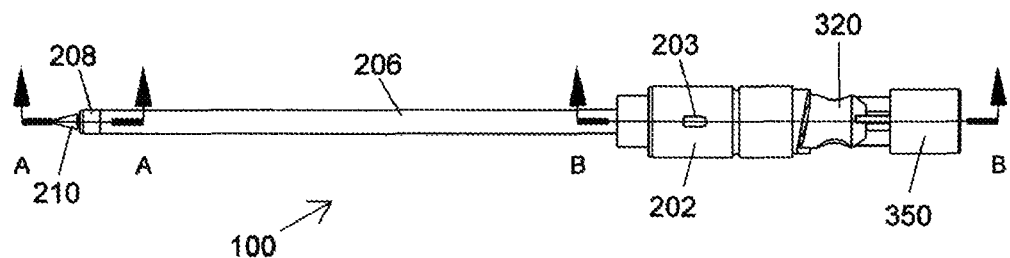
FIG. 16 is a plan view of the objects of FIG. 14.
Figure 17:
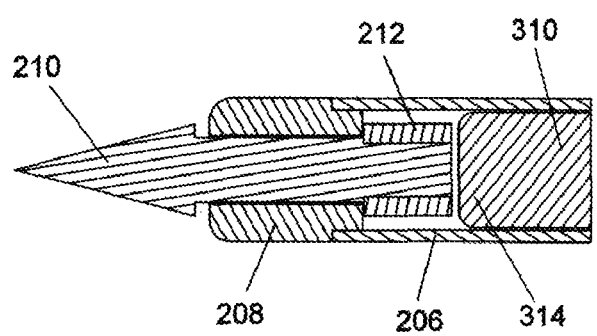
FIG. 17 is an expanded elevational sectional view of the distal portion of the objects of FIG. 16 at location A-A of FIG. 16.
Figure 18:
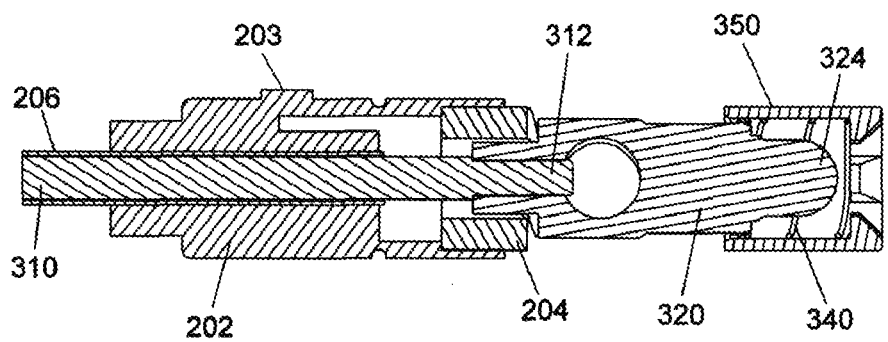
FIG. 18 is an expanded elevational sectional view of the proximal portion of the objects of FIG. 16 at location B-B of FIG. 16.
Figure 19:
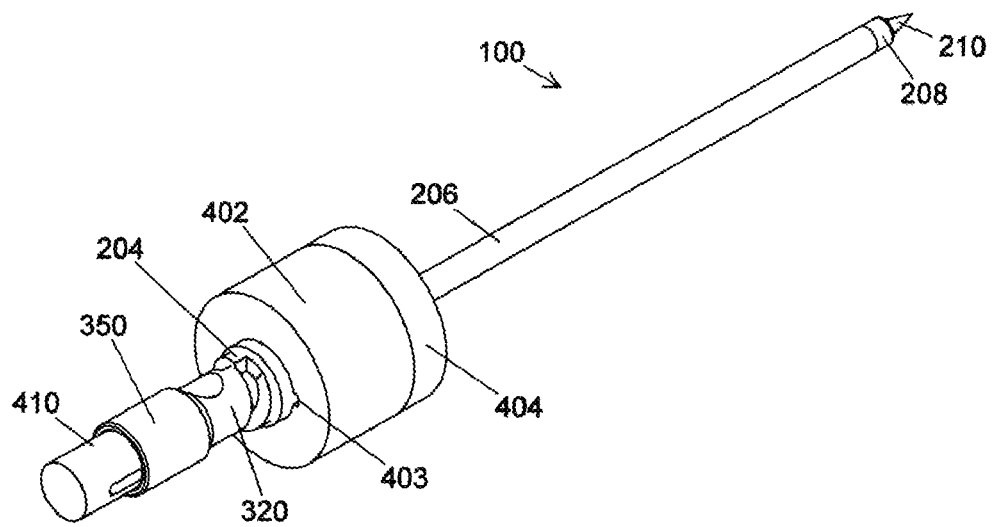
FIG. 19 is a proximal perspective view depicting a surgical percussive driver constructed in accordance with the principles of this invention, such as depicted in FIG. 14, mounted in the distal portion of a conventional arthroscopy shaver handpiece, with the inner assembly coupled to the drive mechanism of the handpiece, and in its retracted (first proximal) position.
Figure 20:
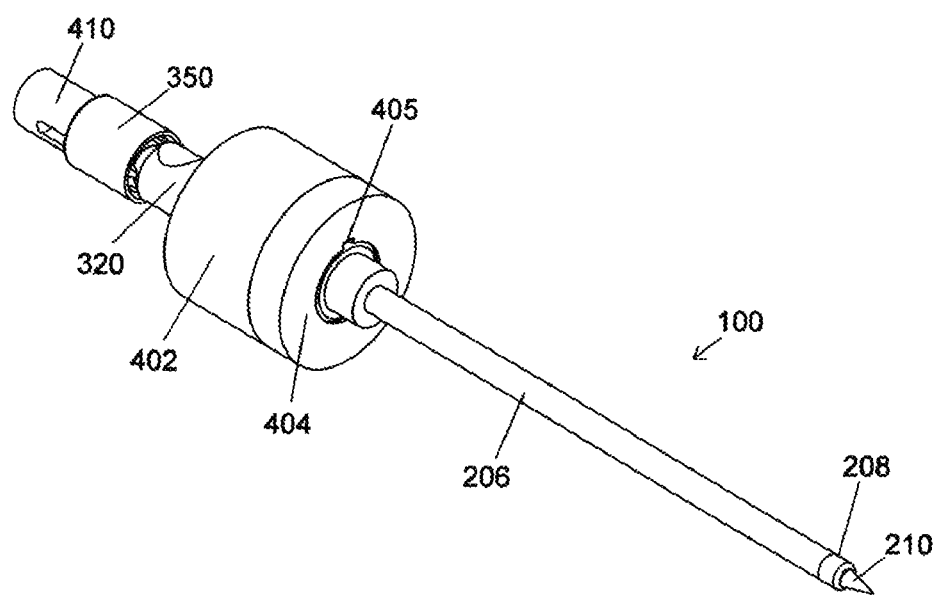
FIG. 20 is a distal perspective view of the objects of FIG. 19.

FIGS. 14 through 18 depict a surgical percussive driver 100 formed in accordance with the principles of this invention and formed of outer assembly 200 and inner assembly 300. Distal rod portion 310 of inner assembly 300 is positioned within tubular distal portion 206 of outer assembly 200 such that inner assembly 300 may be moved axially and rotationally, the axial motion being provided by cooperative interaction of the helical surface of cam 204 of outer assembly 200 and distal helical surface 326 of inner hub 320. The respective helical surfaces (204 and 326) are formed such that rotation of inner assembly 300 within outer assembly 200 causes proximal axial motion of inner assembly 300 a predetermined distance whereupon inner assembly 300 is allowed to return to its distal-most position as depicted in FIGS. 16 through 18. In this distal-most advanced position, metallic distal rod portion forces pointed penetrating element 210 to a distal position, though not its distal-most position.

Figure 21:
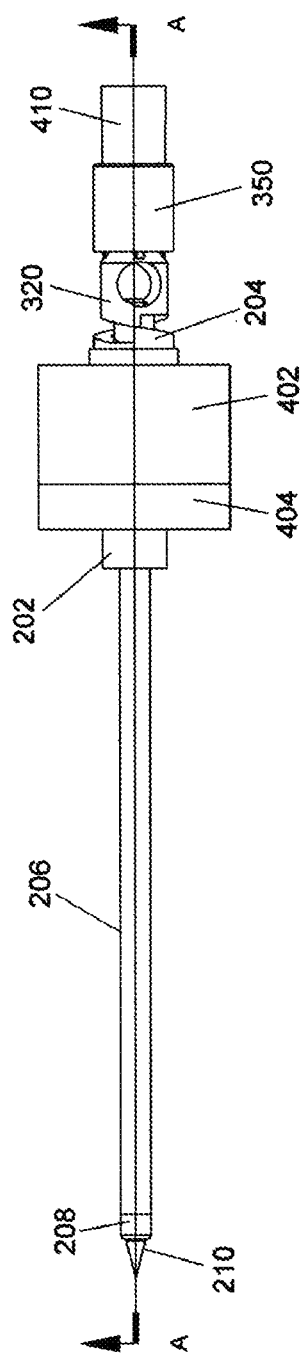
FIG. 21 is a side elevational view of the objects of FIG. 19.
Figure 22:
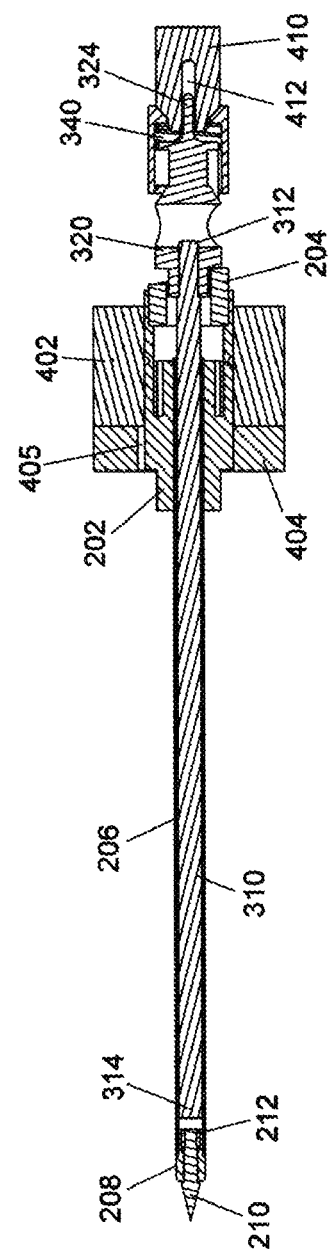
FIG. 22 is a plan sectional view of the objects of FIG. 19 at location A-A of FIG. 21.
Figure 23:
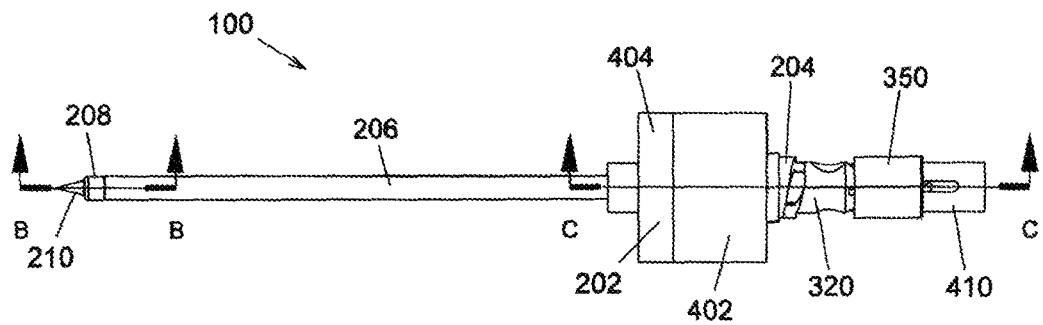
FIG. 23 is a plan view of the objects of FIG. 19.
Figure 24:
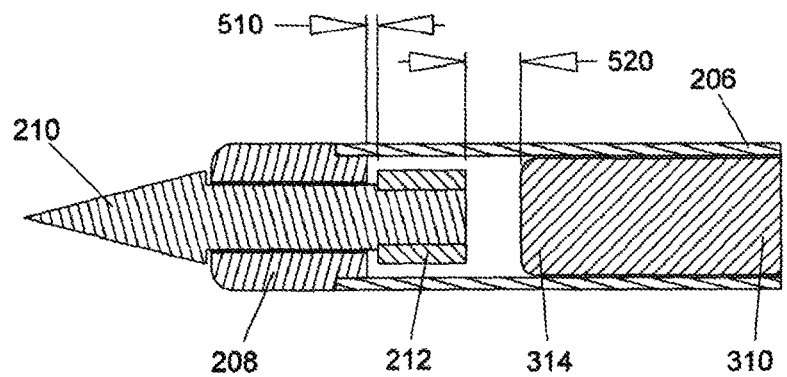
FIG. 24 is an expanded side elevational sectional view of the distal portion of the objects of FIG. 23 at location B-B of FIG. 23.
Figure 25:
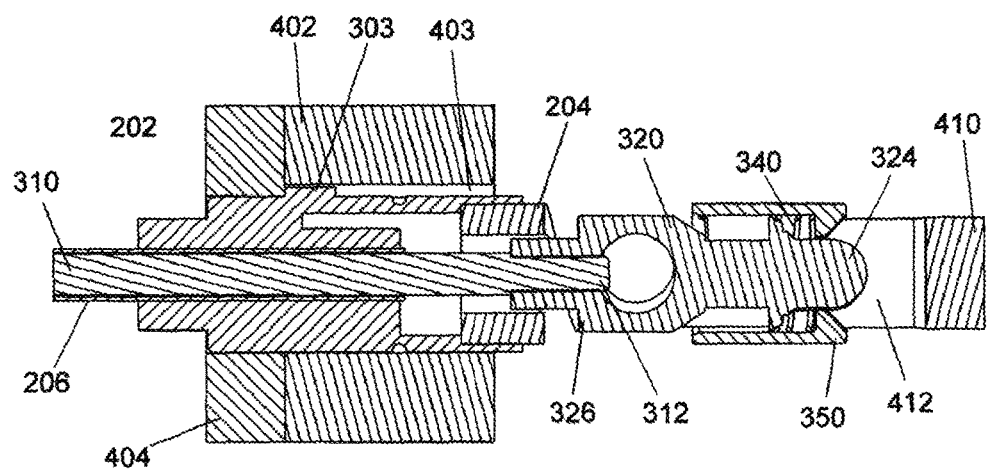
FIG. 25 is an expanded side elevational sectional view of the proximal portion of the objects of FIG. 23 at location C-C of FIG. 23.

FIGS. 19 through 25 present a schematic representation of surgical percussive driver 100 (formed through the coordination of inner and outer assemblies, 300 and 200 respectively) mounted in a conventional arthroscopy shaver handpiece, wherein only those portions of the handpiece essential to the understanding of the operation of device 100 are depicted. Accordingly, fixed element 402 with keyway 403, and rotatable element 404 with keyway 405 are distal elements of a shaver handpiece. In use, rotatable element 404 is positioned such that keyways 403 and 405 are aligned and hub 202 with alignment key 203 can be inserted and positioned as shown in FIG. 25, whereupon rotatable element 404 is repositioned such that keyways 403 and 405 are not aligned and the axial position of hub 202 is maintained in the handpiece. Element 410 corresponds to the rotational drive element of the shaver handpiece. As best seen in FIG. 22 proximal end drive portion 324 of hub 320 is engaged by slot 412 of drive element 410, and the tapered proximal portion of spring retainer 350 engages the tapered distal portion of drive element 410 such that inserting device 100 into the handpiece causes compression of spring 340. The compression of spring 340 is depicted at its near maximum in FIGS. 19 through 25 wherein, as best seen in FIG. 21, the helical proximal surface of cam 204 in cooperative action with helical distal surface 326 of hub 320 has positioned inner assembly 300 at its maximum proximal deflection. Referring to FIG. 24, distal rod portion 310 of inner assembly 300 is positioned proximally a distance 520 from the proximal end of penetrating element 210 and retaining element 212. As shown in FIG. 24, penetrating element 210 is in its proximal-most position with distance 510 between the distal-most surface of retaining element 212 and the proximal-most surface of element 208. Distance 520 is less than the maximum proximal deflection of inner assembly 300 caused by the cooperative action of cam 204 and surface 326 of hub 320. Distances 510 and 520 together are greater than the maximum proximal deflection of inner assembly 300 caused by the cooperative action of cam 204 and surface 326 of hub 320.

Figure 26:
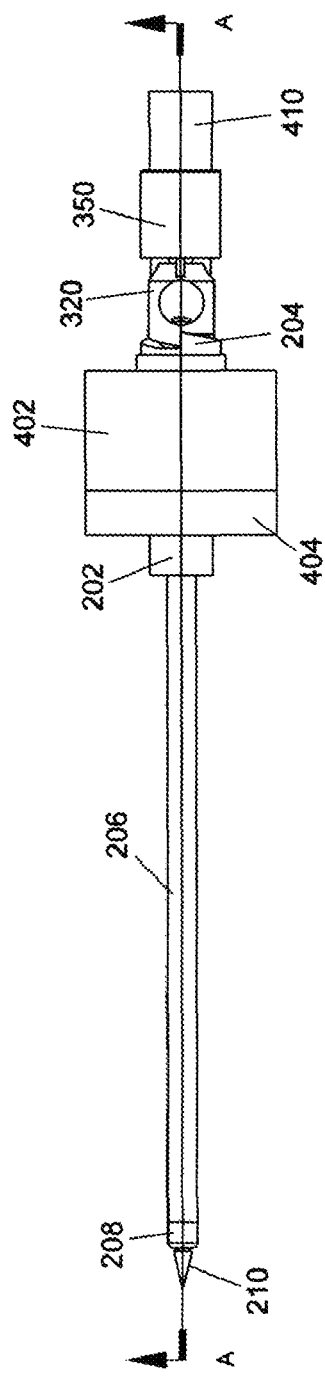
FIG. 26 is a plan view of the objects of FIG. 19 with the inner assembly in the advanced (second distal) position.
Figure 27:
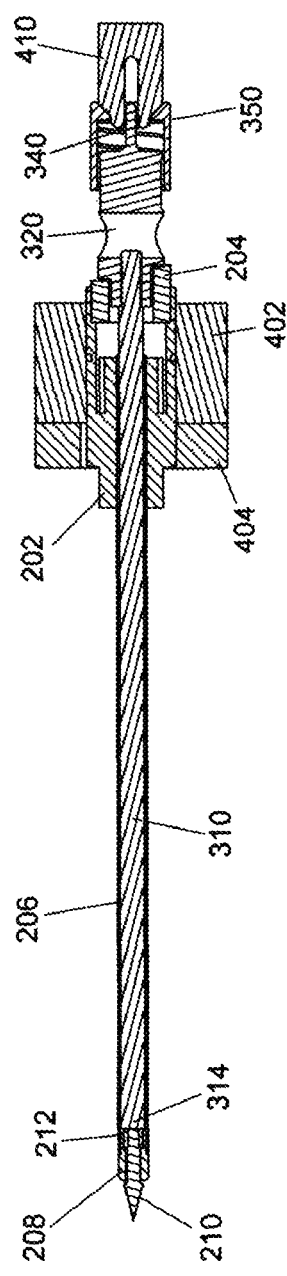
FIG. 27 is a side elevational sectional view of the objects of FIG. 26 at location A-A of FIG. 26.
Figure 28:
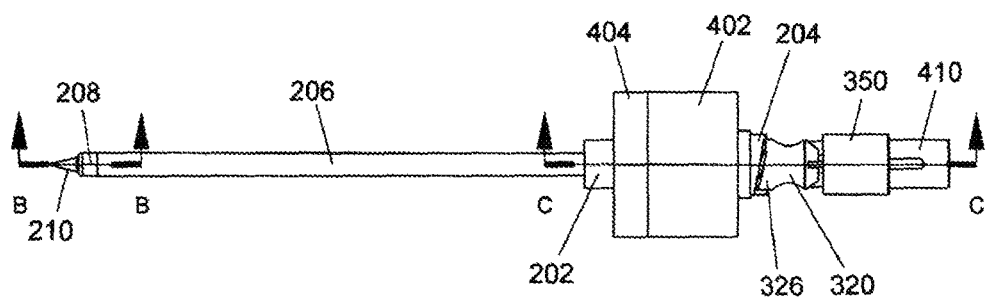
FIG. 28 is a side elevational view of the objects of FIG. 26.
Figure 29:
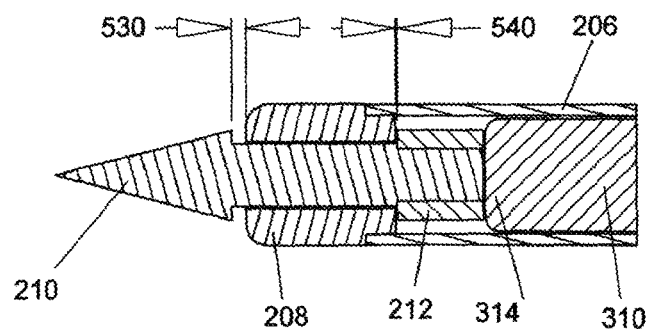
FIG. 29 is an expanded plan sectional view of the distal portion of the objects of FIG. 28 at location B-B of FIG. 28.
Figure 30:
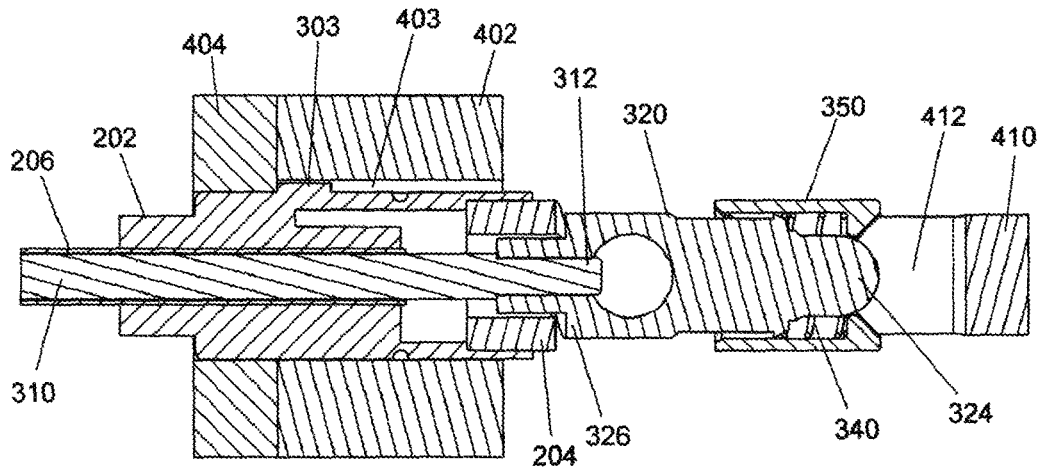
FIG. 30 is an expanded plan sectional view of the proximal portion of the objects of FIG. 28 at location C-C of FIG. 28.

FIGS. 26 through 30 depict the same elements as FIGS. 19 through 25 except that, as best seen in FIG. 26, inner assembly 300 has been rotated such that the helical proximal surface of cam 204 and helical surface 326 of hub 320 are disengaged and inner assembly 300 has traveled to its distal-most position as determined by cam 204 and inner hub 320. When helical surface 326 of hub 320 is rotated past the angular limit of the helical proximal surface of cam 204, force exerted by the (now released) spring 340 causes inner assembly 300 to rapidly travel to its distal limit. Potential energy stored in spring 340 (i.e., kx where k is the spring constant and x is the spring deflection) is converted to kinetic energy (i.e., ½ mv² where m is the mass of the inner assembly and v is the velocity of the inner assembly). As best seen in FIG. 29, the distal end of distal rod 310 of inner assembly 300 contacts the proximal end of penetrating element 210 forcing it distally distance 530.

In use, the pointed distal end of penetrating element 210 is positioned against a bony surface to be penetrated. The shaver handpiece is activated such that inner assembly 300 is rotated, with cam 204 and helical surface 326 of hub 320 causing inner assembly 300 to be repeatedly deflected proximally and allowed to "snap" back to its distal position, in the process transferring its kinetic energy to the penetrating element so as to cause iterative penetration of the bony surface. Device 100 depicts only two such cycles per revolution of inner assembly 300. However, this is meant to be illustrative only; as such other embodiments are contemplated wherein the axial cycles per revolution may range from 1 to 5, preferably 2 to 4, more preferably 2 to 3.

The energy transferred to penetrating element 210 is determined by the spring constant of spring 340. Accordingly, the spring constant can be increased to maximize the energy transferred, the maximum spring constant being determined by the torque required to rotate the inner so as to result in compression of spring 340. The torque required will be determined by the spring constant and by the helical pitch of cam 204 and helical surface 326 of hub 320. This pitch can be minimized by having a single compression of the spring per rotation of inner assembly 300. To increase the rate of penetration of penetrating element 210 into a bony surface, the speed of the handpiece can be increased. The mass of inner assembly 300 ideally should not affect the transfer of the stored spring energy since a lower mass would result in a correspondingly higher velocity; however, the efficiency of the transfer of the kinetic energy and penetration of the bony surface at high velocities may be less efficient. Accordingly, the velocity may be decreased by increasing the mass of distal rod 310 of inner assembly 300 either through maximizing its diameter and length, or by forming it from a high-density metal.

In the embodiment above, spring 340 is retained on inner hub 320 by spring retainer 350. In other embodiments a spring is incorporated in the shaver handpiece and spring 340 and spring retainer 350 are eliminated.

In the illustrative embodiment herein depicted, the penetrating element 210 and distal rod 310 are coaxial. However, other embodiments are anticipated in which the axis of the penetrating element 210 is angularly offset from the axis of distal rod 310, thereby allowing surgeons to penetrate bony surfaces in locations which do not allow coaxial alignment. In such embodiments, the proximal-most surface of penetrating element 210 and retaining element 212 will not be normal to the elements' axis, but rather formed at a predetermined angle such that striking this surface with distal rod 310 produces a penetrating force that is not coaxial with rod 310.

Figure 31:
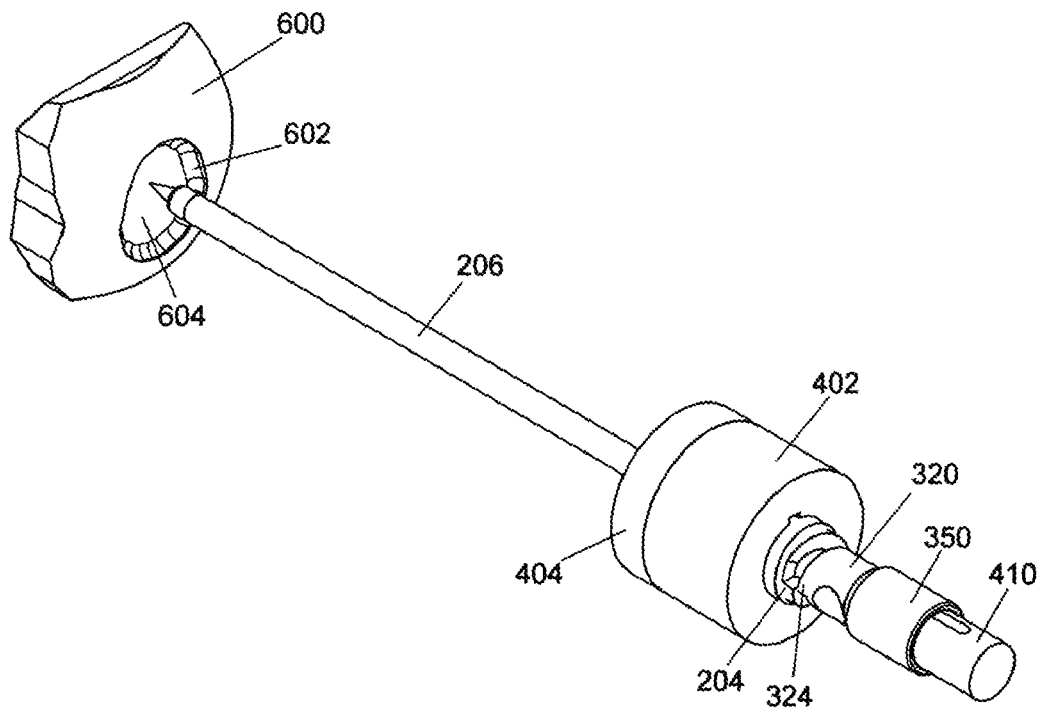
FIG. 31 is a perspective view depicting a surgical percussive driver constructed in accordance with the principles of this invention, such as depicted in FIG. 14, mounted in the distal portion of an arthroscopy shaver handpiece, such as depicted in FIG. 19, and positioned for microfracture treatment of an articular lesion.
Figure 32:
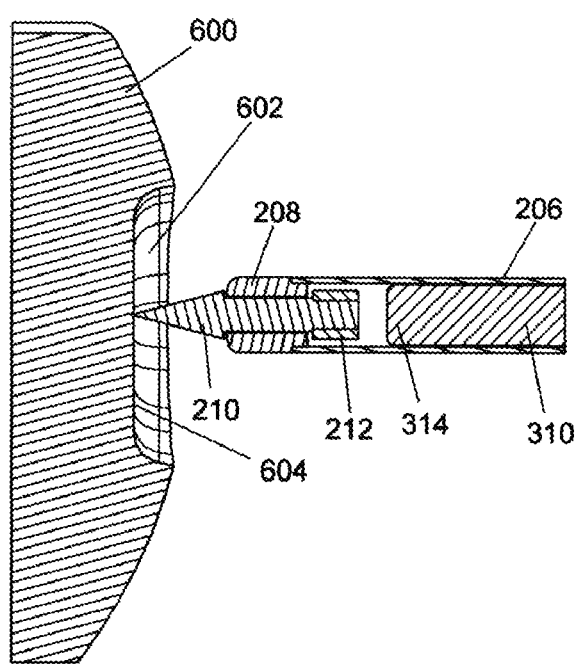
FIG. 32 is an expanded mid-line sectional view of the distal portion of the elements of FIG. 31.
Figure 33:
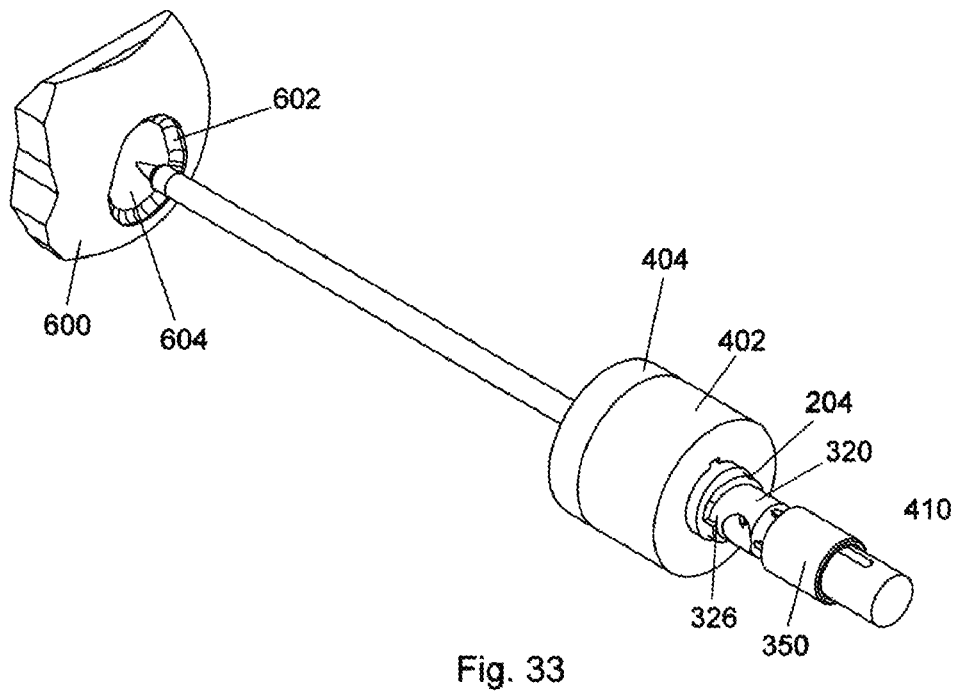
FIG. 33 is a perspective view of the elements of FIG. 31 at the beginning of percussive penetration of the bony surface of the lesion.
Figure 34:
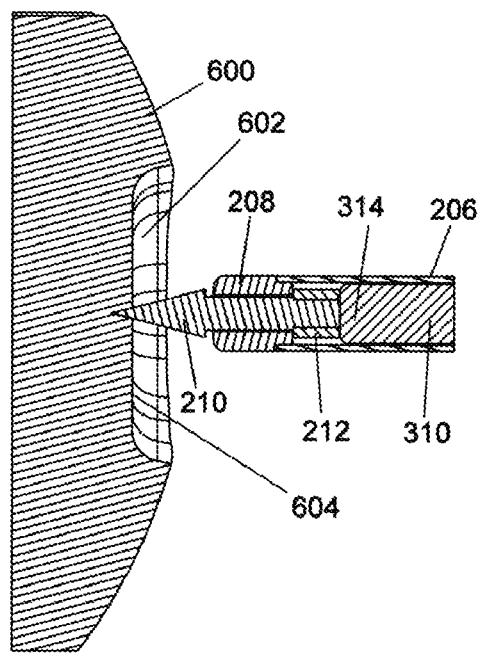
FIG. 34 is an expanded mid-line sectional view of the distal portion of the elements of FIG. 33
Figure 35:
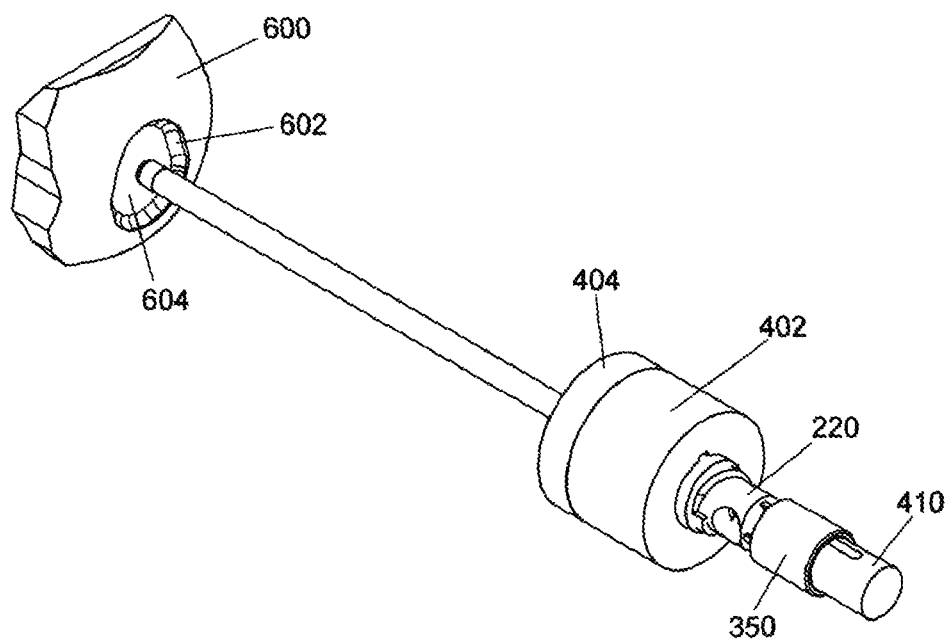
FIG. 35 is a perspective view of the elements of FIG. 31 at completion of percussive penetration of the bony surface of the lesion.
Figure 36:
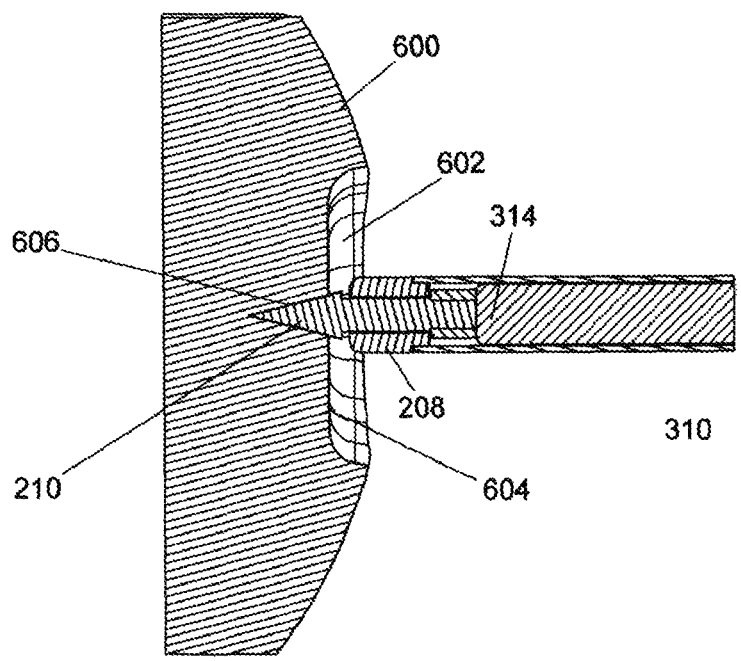
FIG. 36 is an expanded mid-line sectional view of the distal portion of the elements of FIG. 35.
Figure 37:
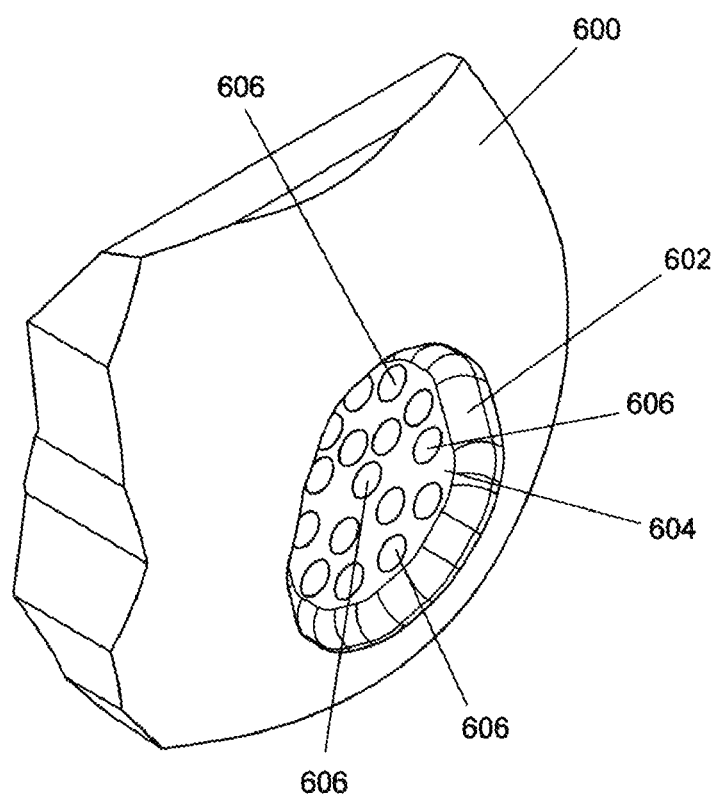
FIG. 37 is a perspective depiction of the articular lesion at completion of microfracture treatment using a percussive surgical instrument of the instant invention.

FIG. 31 depicts surgical percussive driver device 100 positioned for the microfracture treatment of an articular lesion 602 in bone 600. In form, lesion 602 has a form resembling that of a pot-hole. In preparation for treatment, the walls of the "pot-hole" have been cleared back to stable articular cartilage and surface 604 has been abraded using a powered device or curette. As seen in FIG. 32, the distal end of element 210 is placed in contact with surface 604. Rotation of hub 320 and cooperative action between element 204 and surface 324 of hub 320 causes compression of the proximal spring such that distal end 314 of element 310 is displaced proximally from element 312 and the proximal end of element 310. Referring now to FIGS. 33 and 34, continued rotation of hub 320 allows inner assembly 300 to travel distally as stored spring energy is converted to kinetic energy. As best seen in FIG. 34, distal end 314 of rod 310 impacts the proximal end of element 210 and element 212 thereby percussively transferring energy to element 210 causing penetration of surface 604. Continued activation of the shaver handpiece causes repeated percussive transfer of energy to element 210 thereby causing continued penetration of element 210 into surface 604 until element 210 has reached a predetermined depth as depicted in FIGS. 35 and 36 creating conical void 606. The process is repeated so as to form a plurality of conical voids 606 as depicted in FIG. 37.

Figure 38:
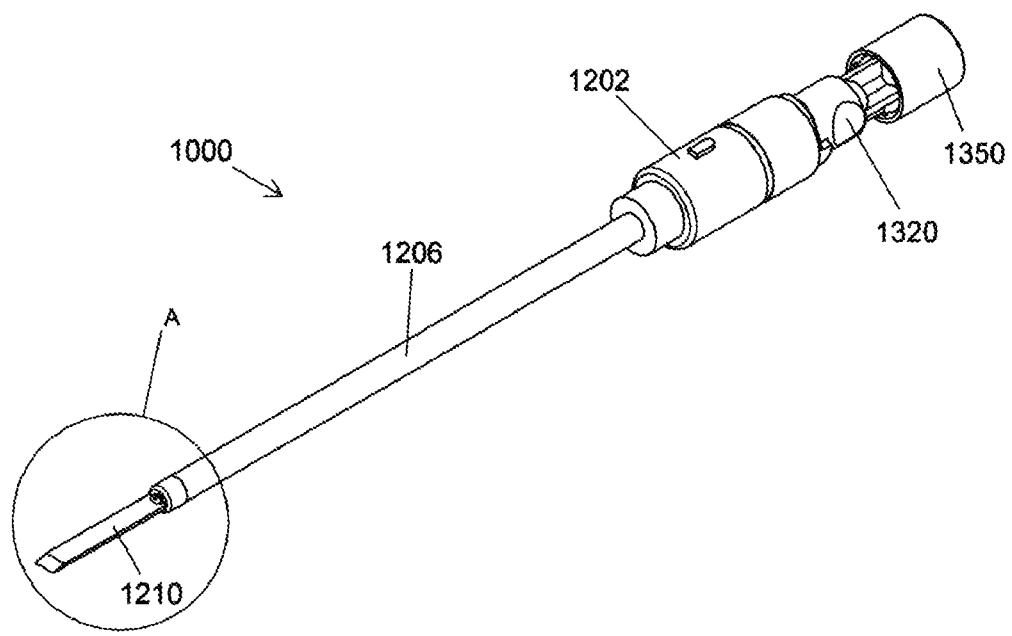
FIG. 38 is a perspective view of an alternate embodiment of the instant invention as illustrated in FIG. 19 in which the distal end is configured for forming flat regions on bony surfaces.
Figure 39:
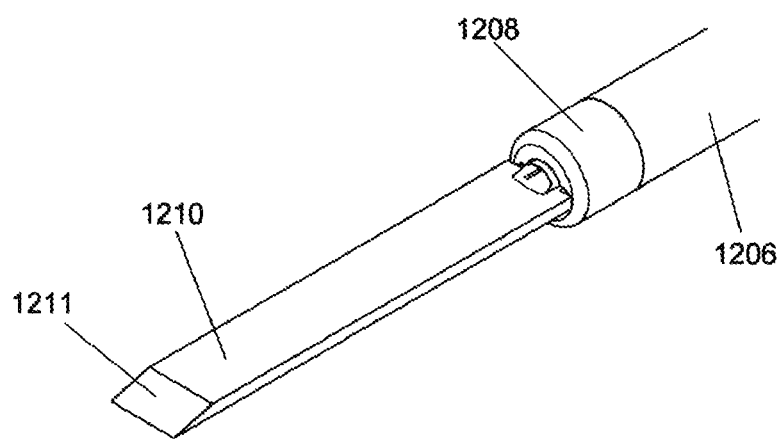
FIG. 39 is an expanded view of the distal portion of the elements of FIG. 38 at location A.
Figure 40:
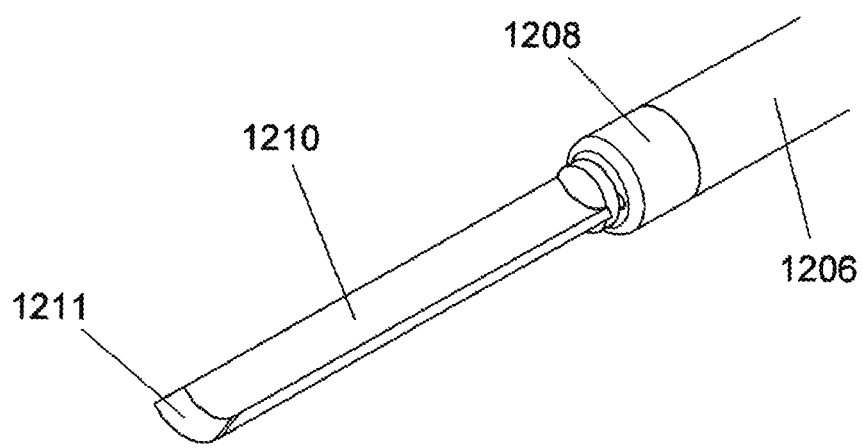
FIG. 40 is a perspective view of an alternate embodiment of the instant invention as illustrated in FIG. 19 in which the distal end is configured for forming grooves in bony surfaces.
Figure 41:
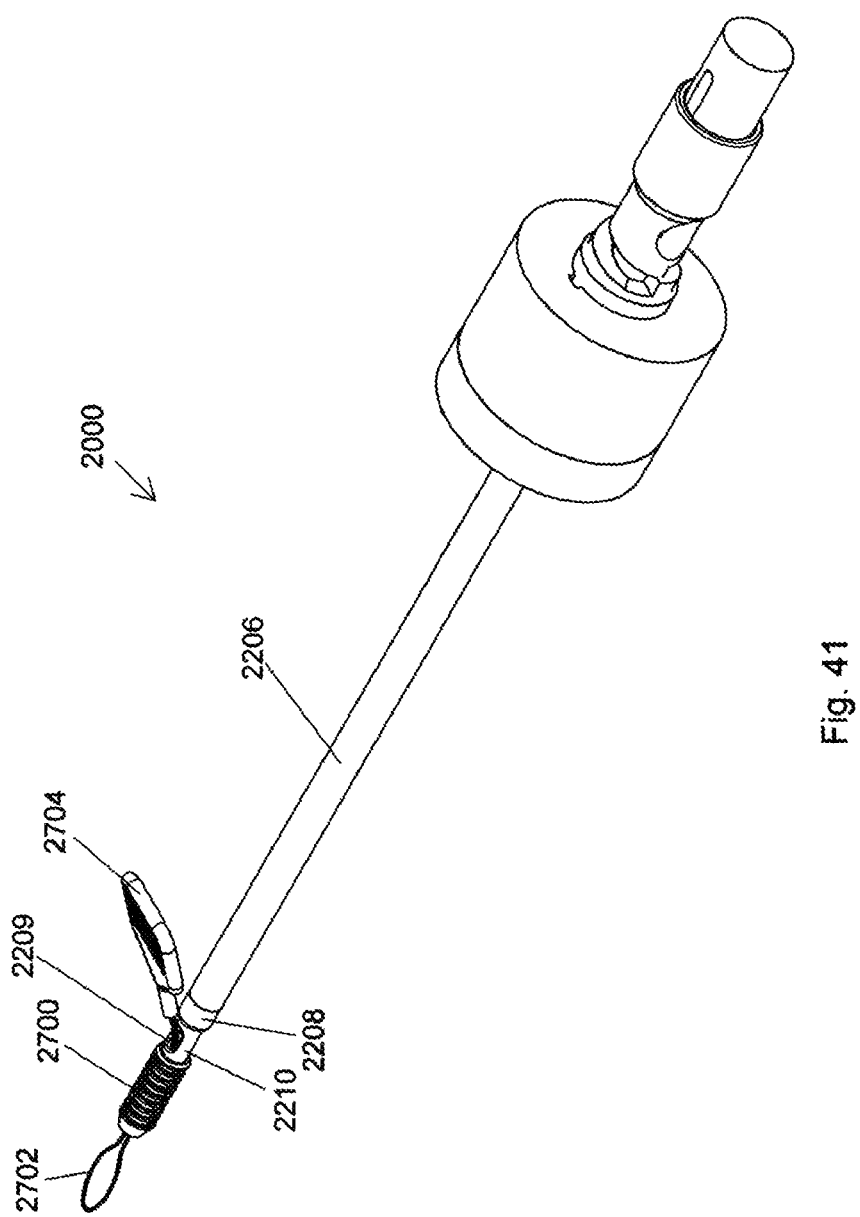
FIG. 41 is a perspective view of an alternate embodiment of a percussive surgical device of the instant invention that is configured for the placement of an interference plug type suture anchor with a loading loop in place for the loading of sutures into the device.
Figure 44:
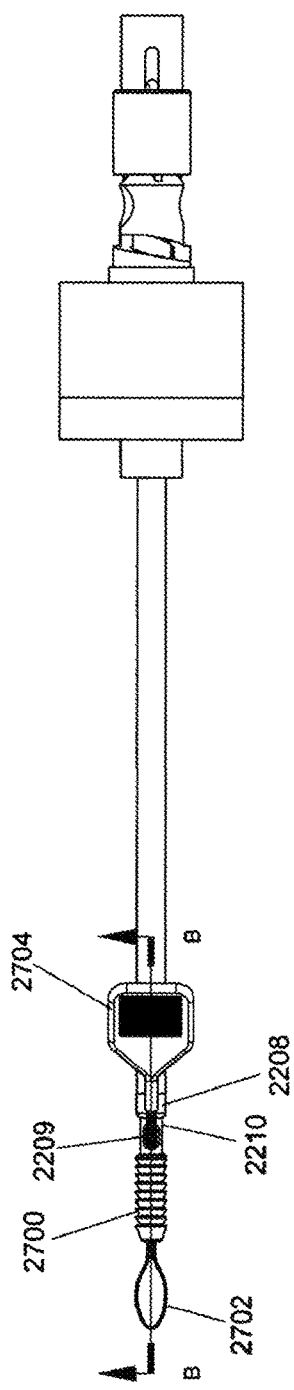
FIG. 44 is a plan view of the objects of FIG. 41.

Percussive surgical devices of the present invention may be advantageously used for a variety of applications and is thus not limited to the application described above. For instance, in an alternate embodiment 1000 depicted in FIGS. 38 and 39, the construction and operation of which are identical to percussive surgical driver device 100 except as described hereafter, distal element 210 with its conically pointed distal portion is replaced by planar elongate distal element 1210 having a sharpened distal edge 1211. Element 1210 functions as a chisel, the percussive energy transferred to it allowing the sharpened distal end 1211 to remove material from bony surfaces so as create flat surfaces. FIG. 40 depicts the distal portion of a similar embodiment in which the elongate element 1210 has a curved cross-section and sharpened distal edge 1211 so as to allow device 1000 to create grooves in bony surfaces.

The use of implants to affix tissue grafts to bone is well known. Common procedures in which such implants (also called "anchors") are used include the repair of rotator cuff tears, and the repair of torn ligaments in the knee, among others. In these procedures, a socket is drilled or punched in the bone at the attachment site and a graft is secured to the bone using an implant placed in the socket. The graft may be secured to the implant by sutures, or an end of the graft may be placed in the socket and secured directly by an implant. Such implants may be threaded and placed in the socket by torque applied to the anchor. Alternatively, the anchor may be an interference plug-type that is not rotated for insertion, but rather forced into the socket by percussive energy that is conventionally supplied by a mallet applied to the anchor driver proximal end.

The placement of an interference plug-type anchor in a prepared socket may be advantageously accomplished using a percussive surgical device of the instant invention. FIGS.

Figure 45:
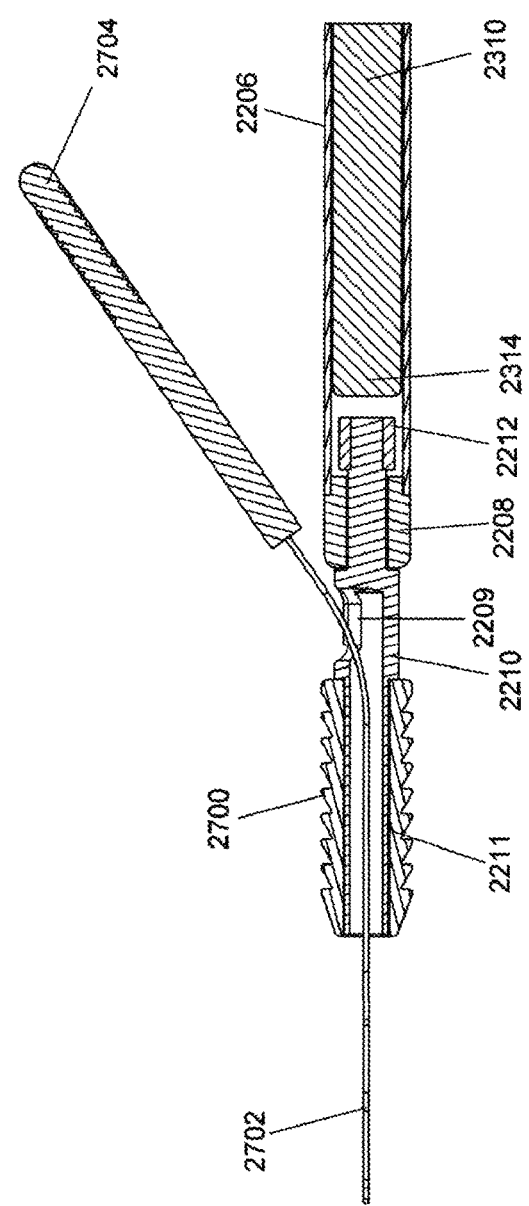
FIG. 45 is an expanded sectional view of the objects of FIG. 44 at location B-B.
Figure 46:
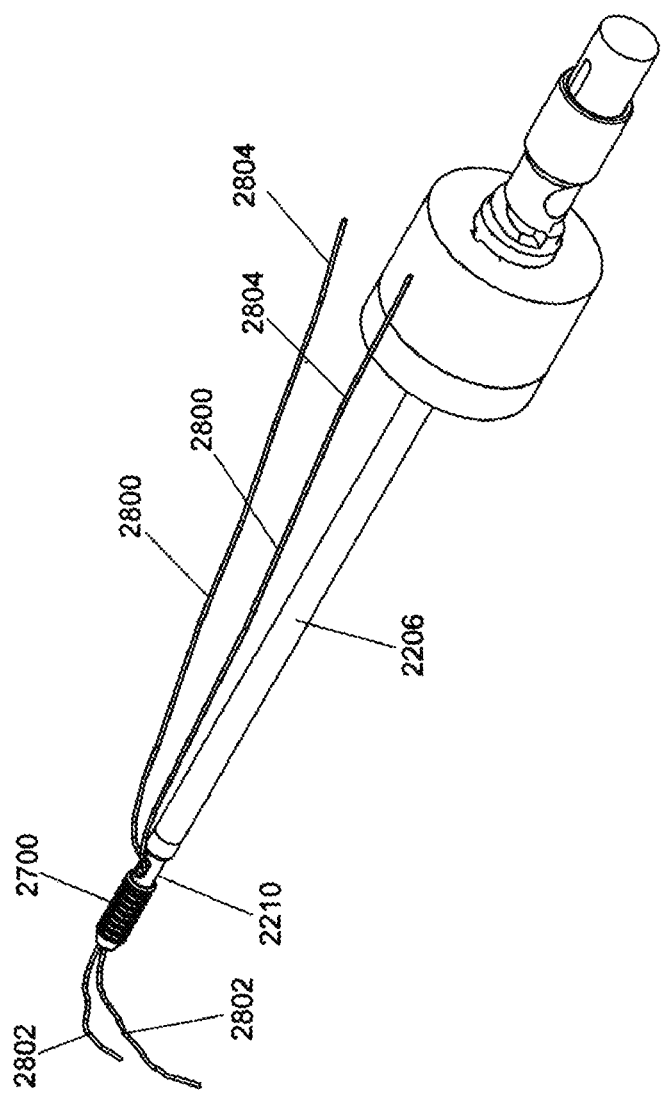
FIG. 46 is a perspective view of the embodiment of FIG. 41 with sutures loaded into the device.

41 through 45 depict device 2000 with interference plug-type anchor 2700 loaded to the distal end thereof in preparation for placement of anchor 2700 in a prepared socket for the purpose of securing a graft. In all aspects of construction and function, device 2000 is identical to device 100 except as subsequently described. As best seen in FIG. 45, distal element 2210 has an elongate cannulated distal portion 2211 on which implant 2700 is positioned, and a proximal lateral opening 2209 in communication with the central lumen of distal portion 2211. Loading loop 2702 is formed from a suitable wire and has formed on its proximal end pull-tab 2704. By placing sutures in loading loop 2702 and withdrawing the loop proximally using pull tab 2704, sutures may be loaded into elongate portion 2211 of distal element 2210 such that the distal portion of the sutures extend beyond the distal end of distal element 2210 and implant 2700, and the proximal portion extends proximally from lateral opening 2209. FIGS. 46 through 49 depict device 2000 with sutures 2800 so loaded there to. Distal portions 2802 of sutures 2800 extend distally beyond the distal end of anchor 2700 and distal portion 2211 of distal element 2210, and proximal portions 2804 extend proximally from lateral opening 2209 of distal element 2210.

Figure 50:
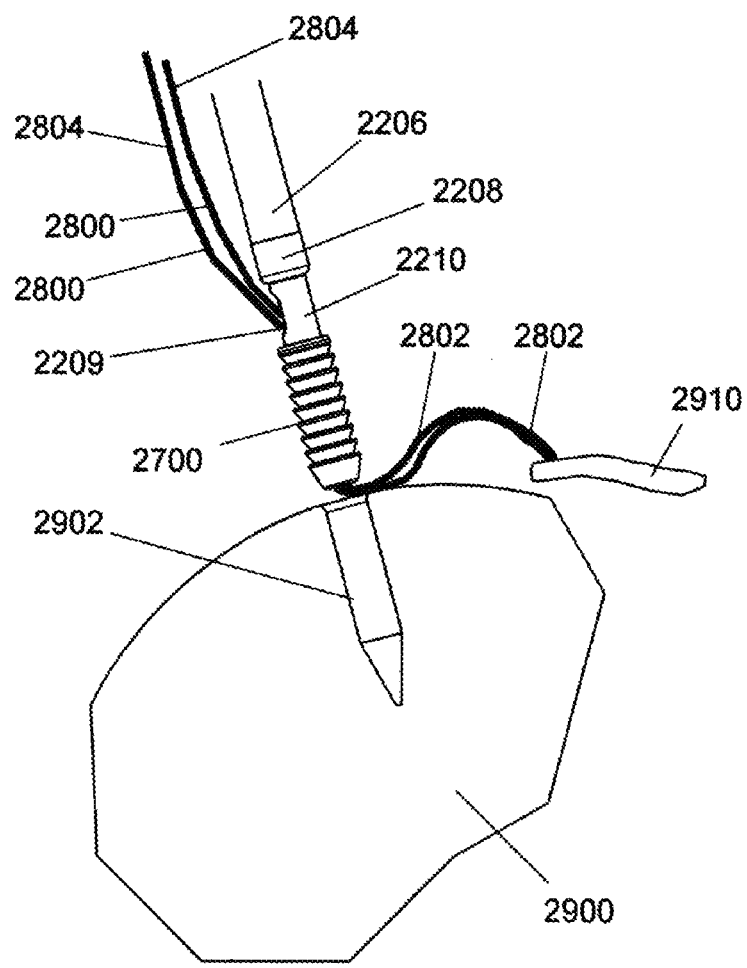
FIG. 50 is a schematic representation of the first step in a procedure for the placement of an interference plug type suture anchor for the purpose of affixing a tissue graft using the embodiment of the instant invention depicted in FIGS. 41 through 49.
Figure 51:
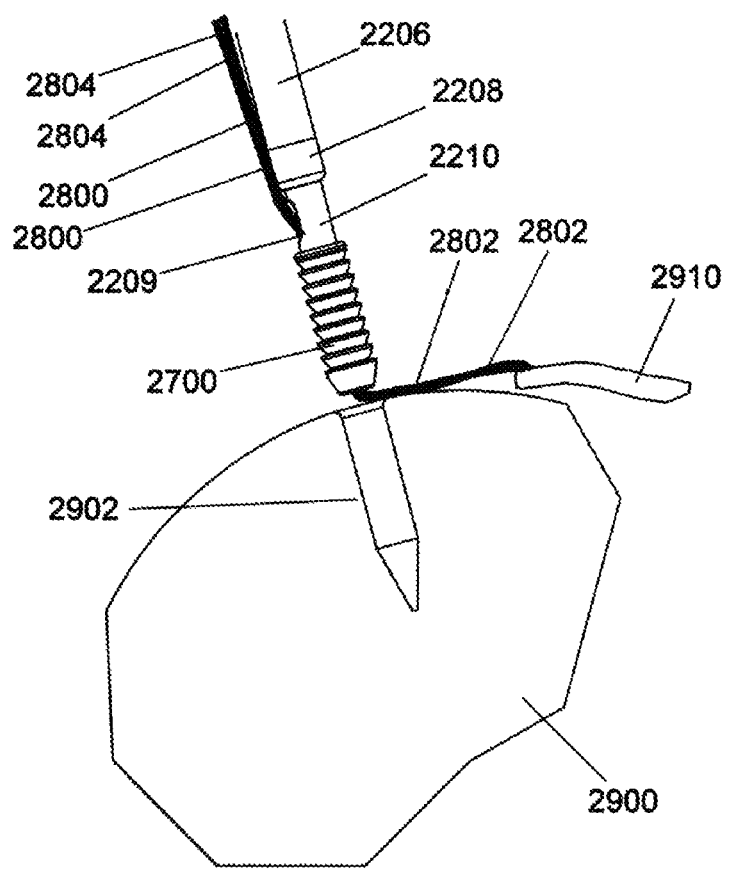
FIG. 51 is a schematic representation of the second step in a procedure for the placement of an interference plug type suture anchor for the purpose of affixing a tissue graft.
Figure 52:
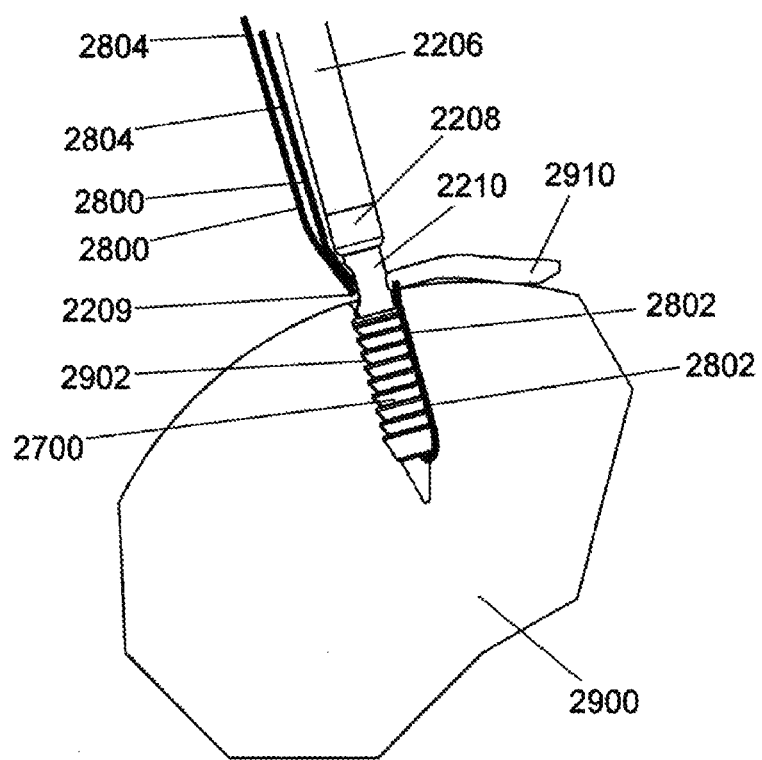
FIG. 52 is a schematic representation of the third step in a procedure for the placement of an interference plug type suture anchor for the purpose of affixing a tissue graft.
Figure 53:
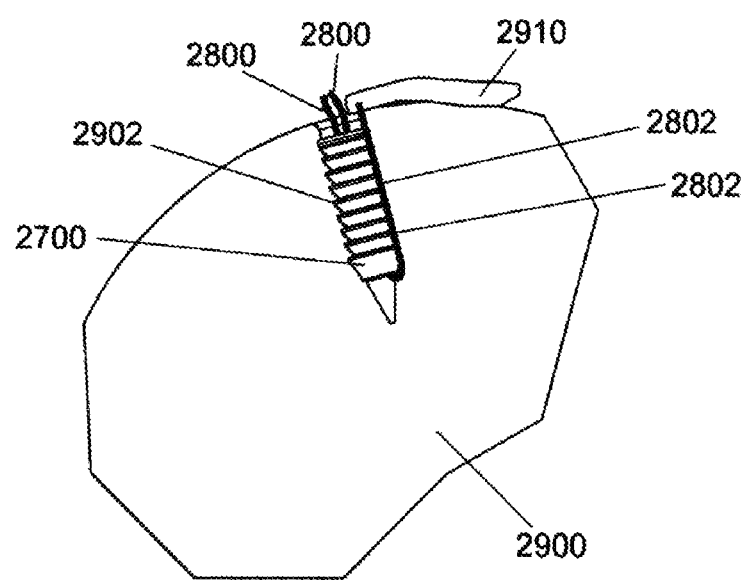
FIG. 53 is a schematic representation of an interference plug type suture anchor placed using the embodiment of the instant invention at the completion of the placement process.
Figure 54:
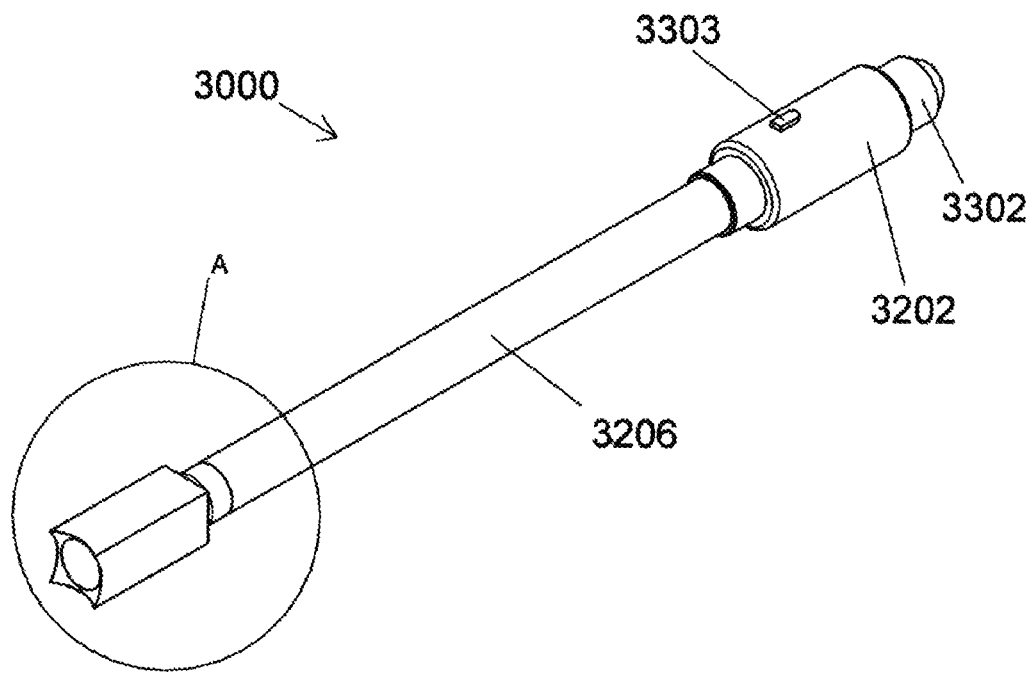
FIG. 54 is a distal perspective view of an alternate embodiment device of the instant invention for use with a handpiece that provides axial percussive energy rather than rotational energy as in the previous embodiments.
Figure 55:
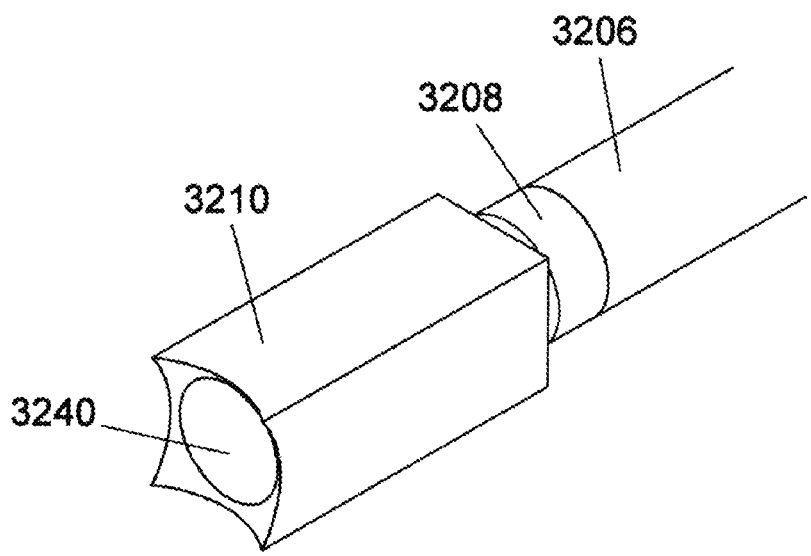
FIG. 55 is an expanded view of the distal portion of the objects of FIG. 54.
Figure 56:
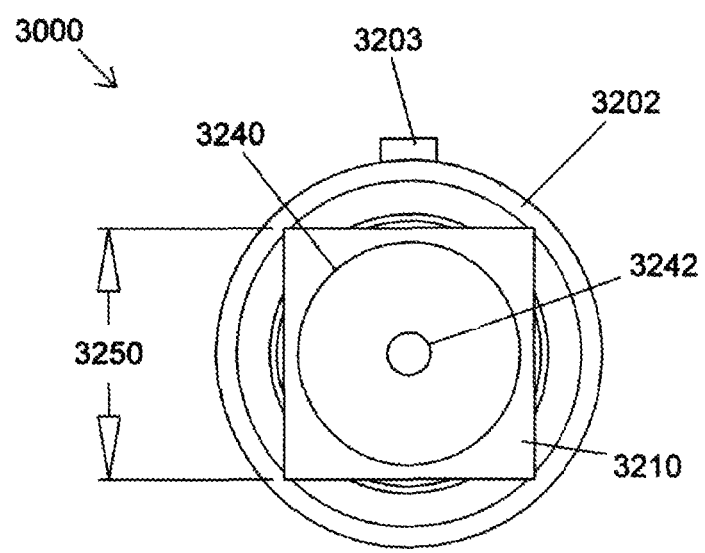
FIG. 56 is a distal axial view of the objects of FIG. 54.

Illustrative steps for placing anchor 2700 in prepared socket 2902 of bone 2900 to affix graft 2910 are depicted in FIGS. 50 through 53. Referring first to FIG. 50, sutures 2800 have been passed through graft 2910 in the usual manner, and loaded into device 2000 in the manner previously herein described such that distal portions 2802 of sutures 2800 are secured to graft 2910, and proximal portions 2804 of sutures 2800 extend proximally from distal element 2210 to outside of the joint space where they may be tensioned by the surgeon. Device 2000 is positioned as depicted in FIG. 50 such that the distal end of anchor 2700 is adjacent to the top of socket 2902. In FIG. 51, the surgeon has applied tension to proximal portions 2804 of sutures 2800 so as to draw graft 2910 into positioned a predetermined distance from socket 2902, the distance being determined such that when implant 2700 is placed in socket 2902, graft 2910 will be in the desired position for fixation. While maintaining tension on sutures 2800 so as to maintain the graft position, the distal end of anchor 2700 is inserted into the socket and, while maintaining slight distal force, the shaver handpiece is activated so as to percussively force implant 2700 into socket 2902. When graft 2910 is at the desired fixation location and implant 2700 is inserted such that its proximal end is below the proximal end of socket 2902, the handpiece is deactivated and anchor placement is complete as depicted in FIG. 52, suture distal portions 2802 being trapped between anchor 2700 and the wall of socket 2902. FIG. 53 depicts the fixation using anchor 2700 with sutures 2800 trimmed just proximal to anchor 2700.

Anchor 2700 is of a type known as a "knotless anchor". When a graft is secured using a knotless anchor, suture are passed through the graft prior to anchor placement and the tying of knots to secure fixation of the graft is not required. Percussive driver device 2000 may also be used for placing anchors in which the sutures are loaded into the anchor before it is placed in the socket, the sutures being subsequently passed through the graft and fixation of the graft achieved through the tying of knots proximal to the anchor and graft.

In the exemplary fixation of graft 2910 using implant 2700 previously herein described, fixation of sutures 2800 is achieved by trapping the sutures between anchor 2700 and the wall of socket 2902. In other embodiments, fixation is achieved by trapping a portion of graft 2910 between anchor 2700 and the wall of socket 2902, a technique known as bio-tenodesis. The placement of anchor 2700 for bio-tenodesis differs from the technique previously herein described in that, instead of leaving a predetermined length of distal suture portions 2802 between the distal end of anchor 2700 and graft 2910, graft 2910 is drawn to the distal end of anchor 2700 by tension applied to proximal portions 2804 of sutures 2800. Thereafter, anchor 2700 and a portion of graft 2910 are inserted into socket 2902 in the manner previously herein described.

Embodiments of the instant invention heretofore described are configured for use with standard shaver handpieces, particularly arthroscopic shavers, wherein the devices of the instant invention convert the rotational motion (and torque) native to the handpiece to axial percussive energy that may be applied to the distal end device component(s). The hubs described herein are standard shaver hubs on which cooperating cam and follower geometries have been formed. The inner assembly is propelled distally by the spring (or other compressible element) that is part of the device assembly. The travel of the inner assembly relative to the outer assembly is limited by the engagement between the inner hub proximal torque transmitting portion and the driving element of the shaver handpiece. The percussive energy transmitted to the distal element of the outer assembly may be increased by increasing the spring constant of the device spring. The maximum percussive energy which may be applied to the distal element is therefore limited by characteristics of the device, i.e. the maximum axial travel of the inner assembly, and the maximum spring constant which the shaver handpiece has sufficient torque to compress.

The present invention contemplates embodiments that utilize a handpiece for driving the device that is not a standard shaver handpiece but rather a handpiece which provides percussive energy rather than rotational energy and is constructed in accordance with principles of the instant invention. Because percussive energy is supplied to the device by the handpiece rather than by conversion of rotational energy to percussive by the device, the amount of percussive energy supplied to the distal element may be much greater. This, in turn, allows the use of larger distal elements that require higher levels of percussive energy to achieve clinical effects.

FIGS. 54 through 60 depict such an alternate embodiment device 3000 configured for use with a handpiece that supplies percussive energy to the proximal end of the inner assembly of the device, the handpiece and device 3000 together forming a percussive surgical system constructed in accordance with the principles of the instant invention. Referring to the figures, device 3000 is alike in construction to embodiments previously herein described, except as subsequently described. Distal element 3210 of device 3000 has a distal portion with a square cross-section, a central lumen 3240, a sharpened distal edge therebetween, and a proximal lumen 3242. As best seen in FIG. 60, inner hub 3302 has no features for torque transmission, being instead configured to provide a means for transmitting proximal spring force from spring 3340 positioned between outer hub 3202 and inner hub 3302 to inner rod element 3310. Referring to FIG. 59, distal element 3210 may move axially within element 3208 distance 3510. In its unconstrained state, distal end 3314 of inner rod element 3310 is displaced distance 3520 from the proximal end of elements 3210 and 3212.

Referring now to FIGS. 61 through 63, which depict device 3000 with corresponding elements of a percussive handpiece, thereby forming a system of the instant invention, drive element 3410 of the handpiece is in its retracted position in preparation for release causing drive element 3410 to travel distally at high velocity so as to cause distal end 3314 of inner element 3310 to impact the proximal end of element 3210 and element 3212 thereby impart percussive energy thereto. Proximal force provided by spring 3340 on hub 3302 and therethrough to inner rod member 3310 maintains contact between the proximal end of member 3310 and drive element 3410 of the handpiece.

Figure 64:
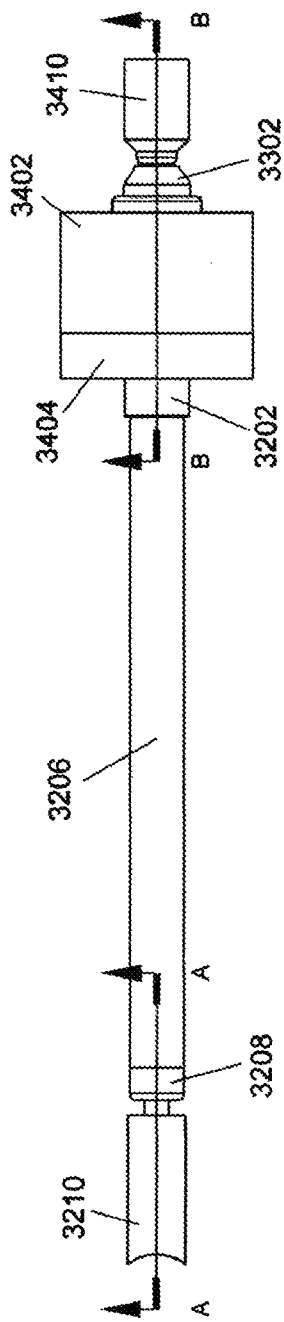
FIG. 64 is a plan view of the embodiment of FIG. 54 with elements of a handpiece configured to supply percussive energy to the device, and with the device in its advanced (second distal) position.
Figure 65:
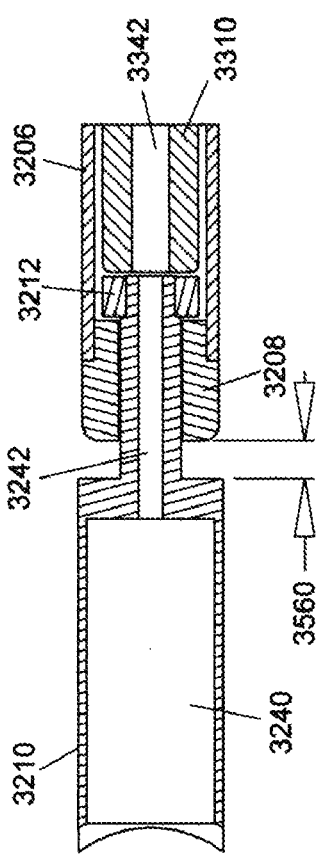
FIG. 65 is an expanded sectional view of the objects of FIG. 64 at location A-A of FIG. 64.
Figure 66:
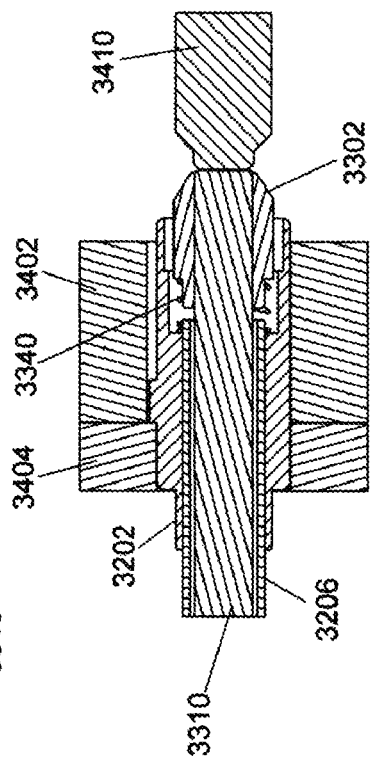
FIG. 66 is an expanded sectional view of the objects of FIG. 64 at location B-B of FIG. 64.
Figure 67:
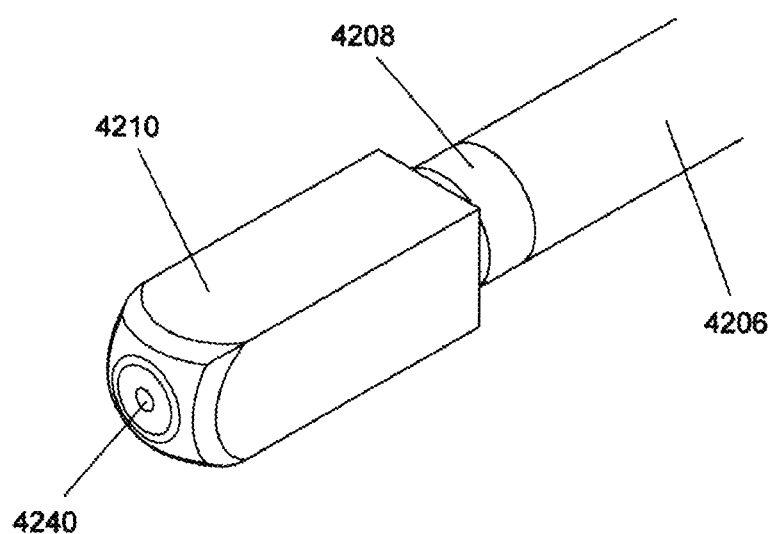
FIG. 67 is a perspective view of the distal portion of an alternate embodiment device of the instant invention.

FIGS. 64 through 66 depict the elements of FIGS. 61 through 63 except as depicted in FIG. 64 through 66 drive element 3410 of the handpiece is at the distal extent of its travel, having imparted percussive energy to rod element 3310 and therethrough to distal element 3210 thereby causing distal element 3210 to travel distally distance 3560. Thereafter drive element 3410 is retracted proximally in the handpiece, spring 3340 maintaining contact between the proximal end of inner rod element 3310 and the distal end of drive element 3410. When drive element 3410 has reached its proximal limit of travel, device 3000 and elements of the handpiece are as depicted in FIGS. 61 through 63. Cycling of the handpiece and device 3000 mounted thereto as herein described results in the repetitive transfer of percussive energy to distal element 3210 so as to allow penetration of element 3210 into a bony surface, or the driving of an implant into a prepared socket as previously herein described. The cycling frequency is preferably between one and ten Hertz, and more preferably between one and five Hertz. In a preferred embodiment the handpiece cycle rate is controlled by the surgeon by means of a proportional control for activation, the cycle rate at full displacement of the control being the device maximum rate. At slight levels of displacement of the activation control the speed is minimal so as to allow a high level of control of the penetration of the distal element 3210.

Distal element 3210 of device 3000 is configured for the forming of square holes in a bony surface, the holes being formed in the following manner. A guide-wire (a small diameter rod) is placed at the desired location. Using a cannulated drill having a diameter equal to lumen 3240 of element 3210, a hole is drilled to a predetermined depth. Thereafter, device 3000 with its associated percussive handpiece is introduced to the site such that the guidewire enters cannulation 3242 of distal element 3210 thereby aligning element 3210 with the drilled hole. The distal sharpened end of element 3210 is then brought into contact with the bony surface and the handpiece activated so as to percussively drive element into the bone so as to create a square hole for the placement therein of a graft.

Distal element 3210 is configured to form a square socket by the removal of material. In an alternate embodiment depicted in FIG. 64, cannulated distal element 4210 is configured to produce a square socket by dilation of the bone adjacent to the previously drilled round hole. That is, instead of removing bone to create the square profile of the socket, bone is compacted to form the corners, the distal end of element 4210 being rounded so as to compact bone rather than sharpened as in element 3210 for the removal of bone. In all other aspects, the embodiment is identical to device 3000.

The ability to form a rectangular or square socket or tunnel is useful for surgeons who use a bone-patellar tendon-bone construct for ACL repair. Currently the graft has trapezoidal bone plugs at its ends when harvested and these bones must be made round to fit into standard round tunnels. Eliminating this rounding step by using square or rectangular tunnels in the repair allows significant savings in procedure time.

INDUSTRIAL APPLICABILITY

As noted previously, the present invention is directed to a surgical assembly having powered driver components that serve to control and automate the application of "percussive force" to the distal end component(s) of the assembly. By automating the percussive force, the present invention not only avoids the present need in the art for a "third hand" but further allows for precisely metered and controlled application of percussive force, thereby minimizing the risk of patient trauma and maximizing device efficiency. Although described in detail with respect to arthroscopic applications, it will be readily apparent to the skilled artisan that the utility of the present invention extends to other minimally invasive endoscopic interventions, particularly with respect to orthopedic procedures such as compound fracture repair and bone grafting.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

The invention has been illustrated by reference to specific examples and preferred embodiments. However, it should be understood that the invention is intended not to be limited by the foregoing description, but to be defined by the appended claims and their equivalents.

What is claimed:

1. A percussive surgical assembly for the placement of a cannulated surgical anchor, wherein said assembly comprises:
   a. an outer assembly characterized by (i) a proximal outer hub having proximal and distal ends, wherein the proximal end of said outer hub includes a first cooperating element, (ii) a distal tubular portion having proximal and distal ends and an elongate lumen extending therebetween, wherein the proximal end of said distal tubular portion is configured to engage the distal end of said outer hub and the distal end of said distal tubular portion includes a distally projecting element positioned and axially movable within said elongate lumen; and (iii) the cannulated surgical anchor mounted about a distal end of said distally projecting element; and
   b. an inner assembly characterized by (i) a proximal inner hub having proximal and distal ends, wherein the proximal end of said inner hub includes a drive portion for transmitting rotational motion from an external shaver handpiece to said inner assembly, and the distal end of said inner hub includes a second cooperating element that engages said first cooperating element, and (ii) a distal portion comprising an elongate driving rod slidably positioned and rotationally and axially movable within said elongate lumen of said distal tubular portion of said outer assembly;

wherein:
   the proximal end of the outer hub is connected to the distal end of the inner hub; and
   the drive portion of the inner hub further comprises an elastic member that transmits an axial force distally on the inner hub to maintain the engagement of said first and second cooperating elements when said inner hub and said outer hub are connected;

whereby:

rotation of the inner assembly relative to the outer assembly drives an interaction between said first and second cooperating elements which causes the inner assembly to move axially from a first extended position to a second retracted position while simultaneously compressing said elastic member; and rotation of the respective inner and outer assemblies past a pre-determined stop limit results in a release of the compressed elastic member, which, in turn, propels the inner assembly in a distal direction such that a distal end of the driving rod strikes a proximal end of the distally projecting element with a percussive force sufficient to move the distally projecting element axially in the distal direction which, in turn, drives said cannulated surgical anchor into a prepared bone socket.

2. The percussive surgical assembly of claim 1, wherein said cannulated surgical anchor comprises an interference plug-type anchor.

3. The percussive surgical assembly of claim 1, wherein said distally projecting element is characterized by a distal opening disposed at the distal end of said projecting element, a lateral opening positioned in a side wall of said projecting element that is fully proximal to said cannulated surgical anchor, and a suture lumen extending between said distal and lateral openings.

4. The percussive surgical assembly of claim 3, wherein said assembly further includes a suture-loading device threaded into said suture lumen, whereby the proximal end of said suture loading device extends through and proximally beyond said lateral opening and the distal end of said suture loading device extends through said distal opening and distally beyond the distal end of said cannulated surgical anchor.

5. The percussive surgical assembly of claim 4, wherein the proximal end of said suture-loading device comprises a pull-tab and the distal end of said suture loading device comprises a suture-loading loop formed from a wire.

6. The percussive surgical assembly of claim 1, wherein said distally projecting element comprises a proximal stop mechanism that constrains the axial movement of said projecting element and prevents it from being dislodged from said elongate lumen.

7. The percussive surgical assembly of claim 1, wherein said elastic member comprises a coiled spring affixed to said inner hub and constrained by a proximal spring retainer.

8. The percussive surgical assembly of claim 1, wherein said first and second cooperating elements comprise complementary cam elements having mating cam follower surfaces.

9. The percussive surgical assembly of claim 8, wherein said cam follower surfaces comprise mating helices.

10. The percussive surgical assembly of claim 1, wherein said first cooperating element comprises a tubular cam element having a helically formed surface on the proximal end of said outer hub and said second cooperating element comprises a helical surface formed on the distal end of said inner hub having a pitch equal to that of the helical proximal surface of said tubular cam element of the outer hub.

11. A percussive arthroscopic shaver-surgical anchor assembly comprising:

a. an arthroscopy shaver handpiece having a distal end defining the opening of a central lumen and a proximal end characterized by a rotational drive element; and b. the percussive surgical assembly of claim 1 assembled to said arthroscopy shaver handpiece, wherein said outer assembly is received within said central lumen such that rotation of said proximal rotational drive element causes rotation of said inner assembly.

12. The percussive arthroscopic shaver-surgical anchor assembly of claim 11, wherein said outer hub is engaged with said arthroscopy shaver handpiece by means of a mating alignment key and keyway.

13. The percussive arthroscopic shaver-surgical anchor assembly of claim 12, wherein said arthroscopy shaver handpiece further comprises a distal rotatable element and a medial fixed element, further wherein said alignment key is disposed on the outer periphery of said outer hub and said mating keyway comprises a notch disposed in the proximal end of said distal rotatable element and extending into said central lumen, wherein rotation of said distal rotatable element disrupts the alignment of said key and keyway and thereby locks the outer assembly to the arthroscopy shaver handpiece so as to prevent relative axial movement thereof.

14. The percussive arthroscopic shaver-surgical anchor assembly of claim 13, wherein assembly of said percussive surgical assembly to said arthroscopy shaver handpiece results in compression of said elastic element.

15. A method for placing a cannulated surgical anchor in a socket prepared in a bony surface in a patient in need thereof using the percussive arthroscopic shaver-surgical anchor assembly of claim 11, said method comprising the step of:

a. introducing said percussive arthroscopic shaver-surgical anchor assembly into a target surgical site comprising the prepared socket of interest;

b. positioning the distal end of said cannulated surgical anchor against said prepared socket;

c. rotating the proximal rotational drive element of said arthroscopic shaver handpiece so as to cause rotation of said inner assembly relative to said outer assembly, which, in turn, causes the inner assembly to axially move from a first extended position to a second retracted position while simultaneously compressing said elastic member;

d. continuing to rotate the respective inner and outer assemblies past a pre-determined stop limit so as to cause release of the elastic member, which, in turn, propels the inner assembly in the distal direction such that the distal end of the driving rod strikes the proximal end of the distally penetrating element with a percussive force sufficient to move the distally projecting penetrating element axially in the distal direction which, in turn, drives said cannulated surgical anchor into said prepared socket.

16. The method of claim 15, wherein said cannulated surgical anchor comprises an interference plug-type anchor.

17. The method of claim 15, wherein said distally projecting element includes a distal opening disposed at said distal end, a lateral opening positioned in a side wall of said projecting element that is fully proximal to said cannulated surgical anchor, and a suture lumen extending between said distal and lateral openings.

18. The method of claim 17, further comprising the steps of:

a. threading one or more elongate sutures into and through said suture lumen, such that the proximal end(s) of said suture(s) extend through and proximally beyond said lateral opening and the distal end(s) of said one or more elongate suture(s) extend(s) through said distal opening and distally beyond the distal end of said cannulated surgical anchor;

b. securing the distal end(s) of said one or more elongate suture(s) to a suitable tissue graft;

c. tensioning said one or more elongate suture(s) so as to position said graft a predetermined distance from said cannulated surgical anchor.

19. The method of claim 18, wherein the step of driving said cannulated surgical anchor into said prepared socket results in a distal portion of said sutures being trapped between said anchor and a wall of said prepared socket.

20. The method of claim 18, wherein the step of driving said cannulated surgical anchor into said prepared socket results in the trapping of a portion of said tissue graft between said anchor and a wall of said prepared socket.

21. The method of claim 18, wherein said one or more sutures are threaded into and through said suture lumen by means of a suture-loading device characterized by:

i. a proximal end comprising a pull tab,
   ii. a distal end comprising a suture-loading loop; and
   iii. an intermediate portion extending from said lateral opening, through said suture lumen and out said distal opening.

22. The method of claim 21, further comprising the steps of:

a. placing one or more elongate sutures in said suture-loading loop;
   b. using said pull tab, proximally drawing said suture-loading loop into said distal opening, through said suture lumen, and out said lateral opening so as to thread said one or more elongate sutures into and through said suture lumen;
   c. removing said one or more elongate sutures from said suture loading loop.

\* \* \* \* \*